United States Patent [19]

Asai et al.

[11] Patent Number: 5,536,491
[45] Date of Patent: Jul. 16, 1996

[54] $^{19}$F POLY AZA MACROCYCLIC MRI CONTRAST MEDIUM

[75] Inventors: Hiroyuki Asai; Tetsuro Kawanaishi, both of Kanagawa-ken, Japan

[73] Assignee: Terumo Kabushiki Kaisha, Tokyo, Japan

[21] Appl. No.: 252,655

[22] Filed: Jun. 1, 1994

[30] Foreign Application Priority Data

Jun. 3, 1993 [JP] Japan .................................. 5-133547
Dec. 22, 1993 [JP] Japan .................................. 5-324149

[51] Int. Cl.$^6$ ............................................. A61B 5/055
[52] U.S. Cl. .................. 424/9.363; 424/9.37; 436/173; 436/806; 540/465; 540/474; 534/16; 514/184; 514/836
[58] Field of Search ........................ 424/9.363, 9.37; 436/173, 806; 540/465, 474; 534/16; 514/184, 836; 128/653.4, 654

[56] References Cited

U.S. PATENT DOCUMENTS

| | | | |
|---|---|---|---|
| 4,714,607 | 12/1987 | Klaveness | 424/9 |
| 5,130,119 | 7/1992 | Blaszkiewicz et al. | 424/9 |
| 5,196,348 | 3/1993 | Schweighardt et al. | 436/173 |
| 5,248,498 | 9/1993 | Neumann et al. | 424/9 |
| 5,318,770 | 6/1994 | White et al. | 424/9.37 |
| 5,324,503 | 6/1994 | Lin et al. | 424/5 |
| 5,342,609 | 8/1994 | Meeh et al. | 424/9 |
| 5,344,640 | 9/1994 | Deutsch et al. | 424/9 |
| 5,358,704 | 10/1994 | Desreux et al. | 424/9 |
| 5,368,840 | 11/1994 | Unger | 424/9 |
| 5,401,493 | 3/1995 | Lohrmann et al. | 424/9 |

FOREIGN PATENT DOCUMENTS 10481420  10/1991  European Pat. Off. .
0592306  10/1993  European Pat. Off. .

OTHER PUBLICATIONS

Prasad, J. S. et al., "Synthesis of Gadolinium Racemic-10-1 Hydroxypropan-2-yl-1,4,7,10-Tetraazacyclododecane-1, 4,7-Triyltriacetate via Tribenzyl-1,4,7,10-Tetraazacyclododecane-1,4,7-Tricarboxylate." Royal Society of Chemistry, Perkin Transactions 1, No. 12, pp. 3329–3332, 1991.

Jackels, S. C. et al., "Paramagnetic Macrocyclic Complexes as Contrast Agents for MR Imaging: Proton Nuclear Relaxation Rate Enhancement in Aqueous Solution and in Rat Tissues." Radiology, 1986, vol. 159, No. 2, pp. 525–530.

Young, S. W. "Nuclear Magnetic Resonance Imaging—Basic Principles." New York: Raven Press, 1984, pp. 112–116.

Databse WPI, Section Ch, Week 8941. London, GB: Derwent Publications Ltd., Class B03, AN 89-297827 and JP-A-1 221 370 (Tosoh Corp) 4 Sep. 1989 (abstract) and Patent Abstracts of Japan, vol. 13, No. 536 (C-660), 29 Nov. 1989 (abstract).

Daly, P. F. et al., "Magnetic Resonance Spectroscopy of Tumors and potential in Vivo Clinical Applications: A Review." Cancer Research, 1989, vol. 49, No. 4, pp. 770–779.

*Primary Examiner*—Gary E. Hollinden
*Attorney, Agent, or Firm*—Burns, Doane, Swecker & Mathis

[57] ABSTRACT

A $^{19}$F-MRI contrast medium for MRI using $^{19}$F as a detectable nucleus, comprising a metal complex compound in which a macro-cyclic polyamine ligand containing not less than one fluorine atoms is coordinate-bonded to a paramagnetic metal ion. Also disclosed is a specific polyamine metal complex compound suitable for the $^{19}$-F-MRI contrast medium.

22 Claims, No Drawings

5,536,491

$^{19}$F POLY AZA MACROCYCLIC MRI CONTRAST MEDIUM

BACKGROUND OF THE INVENTION

1. Field of the Invention

The present invention relates to an MRI contrast medium and, more particularly, to an MRI contrast medium using fluorine as a detectable nucleus.

2. Description of the Related Art

Magnetic resonance imaging (to be referred to as MRI hereinafter) is one of imaging diagnoses, like X-ray imaging, ultrasonic imaging, and nuclear medicine imaging. These imaging diagnoses can visually image pathological changes of living bodies. The imaging diagnoses are, therefore, very excellent means for making accurate diagnoses of diseases and are already used extensively. Among other imaging diagnoses, MRI is a promising imaging diagnosis which has been rapidly spread and developed in recent years.

MRI which is currently being employed in clinical examinations uses $^1$H as a detectable nucleus. A measurement target in such MRI is primarily water molecules which exist in a large amount in a living tissue. The principle of this $^1$H-MRI is as follows.

The relaxation time, the $^1$H density, the $^1$H chemical shift, and the like of $^1$H constituting a water molecule change depending on an environment in which the water molecule is present. In particular, water molecules present in different tissues of a living body can be distinguished from each other by the difference in relaxation time of $^1$H between the water molecules. Therefore, by measuring the relaxation time of $^1$H for many water molecules distributed in a living body and imaging the differences in relaxation time between these water molecules, various tissues of the living body can be imaged. Likewise, it is also possible to distinguish a water molecule in a pathologically abnormal tissue from a water molecule in a normal tissue in accordance with the difference in relaxation time of $^1$H between these water molecules, and so the pathologically abnormal tissue shows an MRI image different from that of the normal tissue. Therefore, pathological abnormalities can be diagnosed on the basis of MRI images.

Recently, on the other hand, MRI diagnoses using nuclides other than $^1$H as detectable nuclei are also being attempted. Examples of the nuclide other than $^1$H, which are NMR-spectroscopically detectable, are $^{19}$F, $^{23}$Na, $^{31}$P, and $^{13}$C. When the relative sensitivity and the isotope abundance are taken into account, however, nuclides practically applicable to the MRI diagnoses are $^{19}$F and $^{31}$P. These two nuclides have already been researched for clinical applications. An example of the applications examined is MRS (magnetic resonance spectroscopy) using $^{31}$P as a detectable nucleus to observe the distribution of ATP, ADP, creatine phosphate, inorganic phosphoric acid, and the like in a living body and use the observation result in diagnoses. Since, however, the sensitivity of $^{31}$P is low, 6% that of $^1$H, $^{31}$P has its measurement limit, and this makes imaging using $^{31}$P difficult. Therefore, clinical applications of $^{31}$P are also limited.

$^{19}$F, in contrast, has the following characteristics and hence is considered as a nuclide with the highest possibility of being applied to clinical examinations.

(1) $^{19}$F has a high sensitivity, 83% that of $^1$H.

(2) Since the resonance frequency of $^{19}$F is close to that of $^1$H, measurements can be performed by using an MRI apparatus for $^1$H.

(3) $^{19}$F is an inexpensive element with a natural abundance of 100%.

(4) $^{19}$F does not exist in any living tissues but teeth. This makes it possible to perform imaging diagnoses using $^{19}$F as a tracer by using a fluorine-containing compound as a contrast medium.

(5) It is also possible to obtain functional information, such as the biochemical environment and the metabolic state of a living tissue, from a change in biochemical the chemical shift of $^{19}$F. This purpose may be accomplished by using a contrast medium compound containing $^{19}$F, the chemical structure of which changes in accordance with changes in the biochemical environment and metabolic state of a living body, and which consequently changes the chemical environment surrounding $^{19}$F.

As described above, $^{19}$F-MRI has characteristics entirely different from those of the conventional $^1$H-MRI and can obtain new information useful in diagnoses. The MRI using $^{19}$F therefore has an extremely high utility value.

For example, when a fluorine compound having compatibility with blood is used as a contrast medium, a portion where a blood flow is present can be selectively imaged. This selective imaging of a blood flow is applicable to identification of an ischemia portion or a necrosis tissue. In addition, selective imaging of a particular tissue is possible when a substance which specifically recognizes a particular organ, a particular lesion, or a particular receptor is labeled with fluorine and used as a contrast medium.

Researches for applying the MRI diagnosis using $^{19}$F as a detectable nucleus to clinical examinations on the basis of the above potential utility value have already been reported or disclosed. Some of these researches are exemplified below.

(a) Attempts to image blood vessels or organs by administering, as a contrast medium, perfluorocarbon which has been used for artificial blood [Investigative Radiology, 20, 504–509 (1985); Investigative Radiology, 23, S298–S301(1988); Journal of Computer Assisted Tomography, 9(1), 8–5 (1985)].

(b) Imaging of the difference between oxygen concentrations in a living body as contrast by using perfluorotripropylamine as a contrast medium [Magnetic Resonance Imaging, 5, 279–285 (1987)].

(c) Imaging of the brains of rats by using well-known 2-fluoro-2-deoxy-D-glucose as a contrast medium in PET (Positron Emission Tomography) [Magnetic Resonance Imaging. 6, 633–635 (1988)].

(d) Imaging using 5-fluorouracil which is a known anticancer agent [NMR in Biomedicine, (No. 3), 113–120 (1988)].

(e) A method of imaging the pH distribution in a living tissue as the difference in the chemical shift of $^{19}$F by using a fluorine-substituted benzene derivative [U.S. Pat. No. No. 5,130,119].

(f) A method of specifically imaging a tissue, such as a cancer lesion, by using an antibody modified with 100 or more fluorine atoms [Jpn. Pat. Appln. KOKAI Publication No. 63 135337].

In addition to the above examples, a large number of attempts to clinically apply the MRI diagnosis using $^{19}$F as a detectable nucleus have been reported. However, the $^{19}$F-MRI has not spread in clinical diagnoses yet. The primary cause for this is assumed to be the insufficient detection sensitivity of a fluorine compound administered as a contrast medium.

That is, since the detection sensitivity of a contrast medium is insufficient, a high-magnetic-field MRI apparatus which has not been clinically used must be employed in order to obtain enough information for diagnoses. An extremely long imaging time, on the other hand, is required in attempting to obtain enough information by using a clinical MRI apparatus that is normally used instead of the high-magnetic-field MRI apparatus. These situations prevent a wide spread of the $^{19}$F-MRI in clinical examinations.

The use of a large quantity of a fluorine compound may increase the imaging sensitivity. In this case, however, the toxicity of that fluorine compound poses a problem. As an example, in the blood vessel imaging experiment (report example (a) described above) using perfluorocarbon as a contrast medium, it is reported that a large amount of the contrast medium is necessary to obtain high-quality images. An application of such the imaging method to human bodies accompanies a serious problem in respect of toxicity.

In addition, when tissue specific imaging is performed by using, as a contrast medium, a substance which has a specific tissue affinity (e.g., a monoclonal antibody; to be referred as a tissue specific substance hereinafter) modified with fluorine, the contrast with respect to the background is impaired by the use of a large amount of the contrast medium. On the other hand, it is practically impossible to improve the detection sensitivity by modifying this tissue specific substance with a large number of fluorine atoms for the reasons to be explained below. First, it is very difficult in view of the synthesis reaction to perform modification of the substance with such a large number of fluorine atoms. Second, even if the modification is possible, this modification with such a large number of fluorine atoms degrades the tissue specificity of the tissue specific substance and also leads to an increase in toxicity.

SUMMARY OF THE INVENTION

It is the first object of the present invention to provide a $^{19}$F-MRI contrast medium for MRI using $^{19}$F as a detectable nucleus, which has a satisfactory imaging performance within the range of a contrast medium concentration that is physiologically acceptable, and which makes it possible to obtain image information useful in diagnoses even when an MRI apparatus that has been normally used in clinical MRI diagnoses is employed.

It is the second object of the present invention to provide a metal complex compound with fluorine atoms, which is useful as the above $^{19}$F-MRI contrast medium.

The above first object of the present invention is achieved by a contrast medium for MRI using $^{19}$F as a detectable nucleus, comprising a metal complex compound in which a macro-cyclic polyamine ligand containing one or more fluorine atoms is coordinate-bonded to a paramagnetic metal ion.

The above second object of the present invention is achieved by a metal complex compound represented by the following formula (I) and its physiologically acceptable salt:

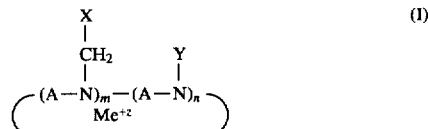

wherein Me, z, A, m, X, n, and Y have the following meanings;

Me: paramagnetic metal ion z: the ionic valence of Me, a positive integer (preferably 2 or 3)

A: which may be the same or different and each represents a group selected from the group consisting of straight chain or branched chain alkylen groups having 1 to 6 carbon atoms, $—(CH_2)_l—O—(CH_2)_l—$, and $—(CH_2)_l—CO—(CH_2)_l—$, wherein l is an integer from 1 to 6 m: an integer from 1 to 6

X: which may be the same or different and each represents a group selected from the group consisting of —COOZ, —PO$_3$HZ, —CONHW, and —OH wherein Z and W are;

Z: a hydrogen atom, an organic or inorganic base equivalent or metal (Me) ion equivalent W: a straight chain or branched chain alkyl group substituted with not less than one —OH group n: an integer from 1 to 6

Y: when n=1, Y is R, wherein R is a substituent which has not less than one fluorine atom and may contain X defined above, and when n=2 or 3, at least one Y is R defined above and each of remaining Y or Ys are —CH$_2$X, a lower alkyl group, or a hydrogen atom.

and wherein a ligand portion of the metal complex compound is coordinate-bonded to the paramagnetic metal ion via at least some of nitrogen atoms and/or oxygen atoms which are contained in the ligand and can be coordinated.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

DETAILED DESCRIPTION OF THE PREFERRED EMBODIMENTS

The principal characteristic feature of the $^{19}$F-MRI contrast medium of the present invention is to use, as a compound having imaging activity, a macro-cyclic polyamine metal complex compound in which a macro-cyclic polyamine ligand containing $^{19}$F is coordinate-bonded to a paramagnetic metal ion.

In the $^{19}$F-MRI contrast medium of the present invention, the paramagnetic metal ion is not particularly limited so far as it has paramagnetism and forms a stable complex. Examples of the paramagnetic metal ion are divalent and trivalent ions of transition metals with atomic numbers 21 to 29, 42, and 44 as well as lanthanoid-series metals with atomic numbers 58 to 70. Of these ions, particularly preferred are ions of chromium, manganese, iron, copper, and gadolinium having stronger paramagnetism.

In the $^{19}$F-MRI contrast medium of the present invention, the macro-cyclic polyamine ligand is an organic ligand containing a plurality of amine nitrogen atoms which can be coordinated to the paramagnetic metal ion. A fluorine atom contained in the macro-cyclic polyamine ligand is the one that has a $^{19}$F nucleus, and it is preferable that a plurality of these fluorine atoms be contained in the ligand. Preferably, the NMR chemical shifts of these fluorine atoms are essentially the same. "The chemical shifts are essentially the same" means that the chemical shift values of all fluorine atoms are distributed within a sufficiently narrow range (preferably within a range of 30 ppm) so that signals from all the fluorine atoms are effectively sampled in MRI measurement and no articraft images are formed.

In the $^{19}$F-MRI contrast medium of the present invention, it is desirable that a tissue specific substance having a specific affinity for a particular living tissue to be imaged is bonded to the macro-cyclic polyamine ligand.

The $^{19}$F-MRI contrast medium of the present invention is desirably prepared into tablets, a powdered medicine, a liquid medicine, and the like according to a given prescription by employing conventional preparation techniques so that the medium is suitably administered to living bodies. In the preparation, it is possible to use assistants or additives that are commonly used in the preparation techniques, such as excipients, stabilizers, surfactants, buffering agents, electrolytes, coloring agents, flavoring agents and taste-conditioning agent.

The $^{19}$F-MRI contrast medium of the present invention has the following advantages.

The first advantage is to be able to significantly amplify the signal intensity in MRI measurement because $^{19}$F and the paramagnetic metal ion exist in the same molecule. This advantage results from the fact that the relaxation time of $^{19}$F is shortened under the effect of the paramagnetic metal. The details of the first advantage will be described below.

The magnetic properties of the paramagnetic metal have an effect on the nuclear spin of $^{19}$F in the vicinity of the metal, shortening the $T_1$ value (longitudinal relaxation time) and the $T_2$ value (transverse relaxation time) in $^{19}$F-NMR. The closer the paramagnetic metal and $^{19}$F, the stronger the effect. In the present invention, since the paramagnetic metal and $^{19}$F exist in the same molecule and are therefore very close to each other, the effect of shortening the relaxation time is extremely large. As a result, in the contrast medium of the present invention, it is possible to obtain very small $T_1$ and $T_2$ values, several milliseconds to several tens of milliseconds, in an aqueous 10 mM solution. Since the $T_1$ and $T_2$ values of a general fluorine compound, such as perfluorocarbon, are on the order of seconds, the relaxation time of $^{19}$F in the contrast medium of the present invention can be largely shortened to $1/100$ to $1/1,000$ under the effect of the paramagnetic metal. Note that the relaxation time of the contrast medium of the present invention remains constant regardless of the concentration of the medium because the paramagnetic metal and $^{19}$F exist in the same molecule. Since the relaxation time is largely shortened as described above, a significantly large signal intensity amplification shown below can be obtained in a pulse sequence of MRI.

When a spin echo method that is clinically most common is used as a pulse sequence method, a signal intensity per pulse is given by the following formula:

signal intensity ∝ F atomic density×exp(−TE/$T_2$)×{1−exp(−TR/$T_1$)}

(where TE is the echo time and TR is the repetition time.)

As is apparent from the above relation, the signal intensity per pulse increases as $T_1$ decreases. Therefore, a significantly high signal intensity per pulse can be obtained when the relaxation time ($T_1$ and $T_2$ values) is largely shortened as described above. In addition, since a short repetition time (TR) of pulse radiation can be set when $T_1$ is shortened, the number of signals that can be extracted in a given unit time increases. This also makes it possible to largely amplify the intensity of a finally extracted signal by integrating a larger number of signals.

In the case of a spin echo method using common imaging conditions, a shorter $T_1$ is more advantageous as described above. In contrast, a shorter $T_2$ is more disadvantageous because the signal intensity in MRI measurement decreases if $T_2$ shortens. As described above, the paramagnetic metal has the effect of shortening the relaxation time substantially evenly on $T_1$ and $T_2$, and so $T_2$ is also shortened significantly in the contrast medium of the present invention. This disadvantage caused by the short $T_2$, however, can be avoided by controlling the imaging conditions. That is, by adopting proper imaging parameters, only the advantage obtained by the short $T_1$ appears significantly, making it possible to perform MRI measurement that does not easily suffer from the disadvantage caused by the short $T_2$. More specifically, the above desirable outcome can be obtained by setting a value of the echo time (TE) as short as possible (preferably a value shorter than T2) and setting the repetition time (TR) at about 1.5 times the value of $T_1$.

Since, however, the setting of the imaging conditions of an MRI apparatus has its limit, the imaging conditions for obtaining the desirable result as described above cannot be adopted in some cases depending on the apparatus and the contrast medium to be used. Especially, in case of using an MRI apparatus having lower limits of TE and TR, it may be impossible to perform the desirable MRI imaging as described above when a contrast medium has an extremely short relaxation time ($T_1$ and T2). Even in such a case, MRI under the above desirable imaging conditions can be performed by using a contrast medium having a longer relaxation time within a range in which the imaging sensitivity does not decrease. It is also an advantage of the present invention to be able to control the relaxation time of a contrast medium which is to be used in this manner. This control of the relaxation time is achieved by molecular design of the macro-cyclic polyamine metal complex compound contained in the contrast medium of the present invention. In the molecular design for controlling the relaxation time of $^{19}$F, the first factor is the type of the paramagnetic metal ion, and the second factor is the distance between the paramagnetic metal ion and $^{19}$F.

The first factor is based on the fact that the effect of shortening the relaxation time is varied depending on the type of the paramagnetic metal ion. The relaxation effect of the paramagnetic metal has correlation with the magnitude of its magnetic moment which is proportional to the number of unpaired electrons that the metal ion has. As an example, the magnitude of the magnetic moment has a sequence of $Cd^{3+}>Mn^{2+}>Cr^{3+}>Fe^{3+}>Cu^{2+}$, and the magnitude of the effect of shortening the relaxation time matches this sequence. In the $^{19}$F-MRI contrast medium of the present invention, therefore, the relaxation time can be controlled by selecting the type of the paramagnetic metal ion. That is, the relaxation time can be shortened by selecting a paramagnetic metal with a large magnetic moment and prolonged by selecting a metal with a small magnetic moment.

The second factor is based on the fact that the relaxation effect of the paramagnetic metal ion has correlation with the distance between the paramagnetic metal ion and $^{19}$F. Therefore, the relaxation time can be prolonged by increasing this distance and shortened by decreasing the distance. The distance between the paramagnetic metal ion and $^{19}$F can be increased easily by inserting an appropriate spacer between the coordination site and the $^{19}$F introduction site of the macro-cyclic polyamine ligand. Such a spacer is not particularly limited, and an alkylen chain or an aromatic ring is usable.

The second advantage of the $^{19}$F-MRI contrast medium according to the present invention is to be able to easily introduce a plurality of fluorine atoms into each molecule of a contrast medium compound. That is, the macro-cyclic polyamine ligand has one or more N atoms to which a substituent can be introduced easily. Therefore, a fluoroalkyl group having one or more fluorine atoms can be introduced to these N atoms so that a plurality of fluorine atoms are contained in one entire molecule. Introducing a plurality of fluorine atoms in this manner makes it possible to obtain more intense MRI signals, improving the detection sensitivity of the contrast medium. This is because the intensity of MRI signals in $^{19}$F-MRI is proportional to the density of fluorine atoms, i.e., the number of fluorine atoms contained in the molecule.

The third advantage is that a plurality of fluorine atoms having essentially the same chemical shift can be introduced easily into the molecule of the contrast medium compound. That is, since the metal complex compound containing macro-cyclic polyamine as a ligand has a good molecular symmetry, a plurality of substitution positions that are essentially the same in chemical shift environment can exist. By using these substitution positions, a plurality of fluorine atoms having essentially the same chemical shift can be introduced into a molecule. The signal sampling efficiency in MRI measurement can be improved because a plurality of fluorine atoms have essentially the same chemical shift. This also effectively prevents, in MRI imaging, formation of chemical shift articraft images that interfere with diagnoses. In contrast, in a conventional contrast medium having a plurality of fluorine atoms, such as perfluorocarbons, the chemical shifts of these fluorine atoms essentially differ from one another. Therefore, it is impossible that signals from all of the fluorine atoms can be sampled effectively. In addition, articraft images are produced.

The fourth advantage of the $^{19}$F-MRI contrast medium according to the present invention is its extremely low toxicity regardless of the presence of metal ions. This results from the fact that the polyamine ligand is an excellent multidentate ligand, as is well known for EDTA, and hence forms a stable complex with metal ions. Many free metal ions exhibit toxicity by interfering with biochemical reactions in living bodies, such as metabolism. Therefore, an instable complex which frees metal ions in a living body shows toxicity caused by these free metal ions. In contrast, many macro-cyclic polyamine metal complexes used in the contrast medium of the present invention have a high complex formation constant ($\log K_{ML}$) of 15 to 25. These values demonstrate that almost no metal ions are freed under the conditions in a living body and hence the metal ions cannot exhibit their toxicity.

The fifth advantage of the $^{19}$F-MRI contrast medium according to the present invention is that the macro-cyclic polyamine metal complex as an imaging active substance can be chemically modified easily. Since a compound having no active reaction site, such as perfluorocarbon, is low in reactivity, it is very difficult to chemically modify such a compound through an usual chemical reaction. The macro-cyclic polyamine metal complex of the present invention, on the other hand, can be easily subjected to various chemical modifications corresponding to intended applications, by using nitrogen atoms present in the macro-cyclic polyamine ligand portion of the complex.

The first objective of such a chemical modification is to impart tissue specificity to the contrast medium of the present invention. For example, organ specificity or lesion specificity can be imparted by controlling the size, the hydrophobic/hydrophilic balance, and the charge of a molecule. A most useful method for this purpose is to form a composite of a macro-cyclic polyamine metal complex and a tissue specific substance having a specific affinity for a particular living tissue. As such a tissue specific substance, there are various known substances such as proteins, sugars, glycoproteins, lipids, and other organic compounds. Practical examples of the tissue specific substance are a monoclonal antibody and its fragment for a particular tissue, hormones, a neurotransmitter, a drug which binds to a particular receptor, an organ cumulative substance, and a metabolic substrate compound. These substances may be either substances originating from living bodies or synthetic substances.

To form a composite of a macro-cyclic polyamine metal complex and a tissue specific substance described above, the tissue specific substance may be combined with the macro-cyclic polyamine ligand via a proper bond, such as an ester bond, an amide bond, an amide bond, or a disulfide bond. For this purpose, a macro-cyclic polyamine metal complex in which an appropriate reactive group is introduced to the ligand portion can be reacted with the tissue specific substance. This causes the reactive group introduced to the ligand portion to react with a reactive group (e.g., an amino group, a thiol group, a hydroxyl group, a carboxyl group, or an imidazole group) contained in the tissue specific substance, forming the bond as described above between them. The reactive group to be introduced to the macro-cyclic polyamine ligand portion is properly selected from, e.g., an acid anhydride group, an acid halide group, an active ester group, a nitrene group, an isocyanate group, an isothiocyanate group, and a maleimide group in accordance with the reactive group contained in the tissue specific substance. The reactive group to be introduced to the ligand portion is preferably introduced while being protected by a proper protective group, and activated by eliminating the protective group immediately before the reaction with the tissue specific substance. If possible, the tissue specific substance may be bonded to the macro-cyclic polyamine metal complex by using a coupling reagent, such as carbodiimide.

Tissue specific imaging is possible by bonding a tissue specific substance to a macro-cyclic polyamine metal complex as described above. Examples of a target tissue in this imaging may be a tumor tissue, an infectious tissue, an inflammatory tissue, a necrotic tissue, a metabolic abnormal tissue, a particular metabolite cumulative tissue, and a particular receptor existing tissue. This tissue specific imaging is extremely useful in MRI diagnoses of various diseases, such as cancers, infectious diseases, ischemic heart diseases, arteriosclerosis, ulcers, and mental diseases. The illustrative details of this tissue specific imaging are as follows.

In specific imaging of a tumor tissue, an antibody whose antigen is a tumor tissue is normally used. A large number of researches on antibodies against a tumor tissue have been reported. Applications of these antibodies to external diagnoses and nuclear medicine have been attempted, and the antibodies have already been used in clinical diagnoses. MRI using such an antibody as the tissue specific substance is useful in diagnoses of, e.g., malignant melanoma, carcinoma of the colon and rectum, pancreatic cancer, and malignant lymphoma. In specific imaging of an inflammatory tissue, a substance having affinity for activated leucocytes which appear in a large number in an inflammatory portion can be used as the tissue specific substance. In addition, leucocytes themselves can be used as the tissue specific substance. To specifically image a necrotic tissue of a cardiac muscle, a monoclonal antibody against myosin can be used as the tissue specific substance.

The above tissue specific imaging can also be applied to receptor mapping by using, as the tissue specific substance, agonist, antagonist, hormone, or a chemical transmitter, each of which acts on a particular receptor, or an antibody against the receptor.

For the purpose of the above tissue specific imaging, a tissue specific substance with the broadest application range is an antibody. An antibody used for this purpose preferably has the following properties.

(1) Having specificity for a target tissue and not having cross reactivity for other tissues. In this respect, a monoclonal antibody is particularly desirable.

(2) Acting on an antigen present at a high concentration in a living body and having a high affinity for that antigen.

(3) Acting on an antigen which exists only in a tissue, such as a cell membrane, and is not freed into blood.

Although an antibody may be used in the form of a whole antibody molecule, it can also be used as an antibody fragment containing an antigen recognizing portion. The use of this antibody fragment provides the following merits. First, since the background signal vanishes rapidly, cumulation in a target tissue can be detected within a short time period. This is because the antibody fragment has a short half life in a living body and hence vanishes rapidly except in a target tissue. Second, the antibody fragment hardly decreases its tissue specificity when used continuously compared to a whole antibody molecule. This is so because an antibody against the antibody fragment is more difficult to be produced than an antibody against a whole antibody molecule. The antibody fragment obtained by removing an Fc portion not participating in antigen recognition from a whole antibody molecule are used frequently. Examples are an Fab fragment obtained by subjecting a whole antibody molecule to a papain treatment, and an F(ab') fragment obtained by performing a pepsin treatment of a whole antibody molecule.

The second object of the chemical modification performed for the imaging active substance (i.e., the macro-cyclic polyamine metal complex) of the present invention is to detect changes of tissue environments, such as a pH, an oxygen concentration and/or an oxidation-reduction potential, by converting the environmental changes into the chemical shift changes of $^{19}F$. This makes it possible to obtain information concerning tissue environments from the chemical shift of $^{19}F$, resulting that imaging of, e.g., an abnormal metabolic tissue becomes possible. An example of such a chemical modification is to introduce a ring structure, which closes or opens depending on the change in pH, into a ligand molecule in the vicinity of $^{19}F$.

As described above, the $^{19}F$-MRI contrast medium of the present invention has a much higher sensitivity and a lower toxicity than those of conventional $^{19}F$-MRI contrast media, such as perfluorocarbon. Therefore, the use of the $^{19}F$-MRI contrast medium of the present invention makes it possible to realize clinical applications of $^{19}F$-MRI, resulting that MRI diagnoses for various purposes entirely different from those of $^1H$-MRI can be made.

For example, the $^{19}F$-MRI contrast medium of the present invention is applicable to image diagnoses which is currently made by means of nuclear medicine, such as blood flow scintigraphy using radioisotopes. That is, the presence of a blood flow can be imaged by administering the $^{19}F$-MRI contrast medium (of a water-soluble type) of the present invention into blood and imaging using the medium as a tracer. Like the blood flow scintigraphy, such an MRI diagnosis is useful in finding a necrotic tissue, determining an ischemic portion, and finding an infarct portion of a blood vessel. In addition, exposure to radiation can be avoided because no radioisotope is used, and there is another advantage that neither a particle accelerator nor an installation for RI experiments is required. Furthermore, image information obtained by $^{19}F$-MRI is superior to that obtained by the method of nuclear medicine, in respect to contrast and resolution in many cases.

The $^{19}F$-MRI contrast medium of the present invention can also be applied to tissue specific imaging and imaging of a functionally abnormal portion, such as a metabolic abnormality, as described above.

Moreover, the macro-cyclic polyamine metal complex used as the imaging active substance in the $^{19}F$-MRI contrast medium of the present invention can be used in the following manner, as well as administering it into a living body as a contrast medium. That is, by coating or mixing the macro-cyclic polyamine metal complex on or into a catheter or an artificial organ, position information of the catheter or the artificial organ can be obtained by using MRI.

A novel macro-cyclic polyamine metal complex for use in the above $^{19}F$-MRI contrast medium will be described below.

The macro-cyclic polyamine complex compound provided by the present invention is a metal complex compound represented by the following formula (I) and its physiologically acceptable salt:

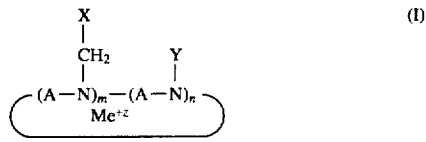

wherein Me, z, A, m, X, n, and Y have the following meanings;

Me: paramagnetic metal ion z: the ionic valence of Me, a positive integer (preferably 2 or 3)

A: which may be the same or different and each represents a group selected from the group consisting of straight chain or branched chain alkylen groups having 1 to 6 carbon atoms, $-(CH_2)_l-O-(CH_2)_l-$, and $-(CH_2)_l-CO-(CH_2)_l-$, wherein l is an integer from 1 to 6 m: an integer from 1 to 6

X: which may be the same or different and each represents a group selected from the group consisting of —COOZ, —PO₃HZ, —CONHW, and —OH wherein Z and W are;

Z: a hydrogen atom, an organic or inorganic base equivalent or metal (Me) ion equivalent W: a straight chain or branched chain alkyl group substituted with not less than one —OH group n: an integer from 1 to 6

Y: when n=1, Y is R, wherein R is a substituent which has not less than one fluorine atom and may contain X defined above, and when n=2 or 3, at least one Y is R defined above and each of remaining Ys is —CH₂X, a lower alkyl group, or a hydrogen atom.

and wherein a ligand portion of the metal complex compound is coordinate-bonded to the paramagnetic metal ion via at least some of nitrogen atoms and/or oxygen atoms which are contained in the ligand and can be coordinated. The paramagnetic metal ion $Me^{+z}$ in the macro-cyclic polyamine metal complex of the present invention has already been described. Nitrogen atoms in the macro-cyclic polyamine ligand and oxygen atoms of the hydroxyl group can contribute to a coordinating bond between the macro-cyclic polyamine ligand and the paramagnetic metal. This hydroxyl group may be either a hydroxyl group contained in X (including X contained in Y) or a hydroxyl group contained in W.

If Z represents an inorganic base or an organic base, the base is used to obtain a complex in the form of a stable neutral salt because toxicity can be reduced in some cases by making the complex into the form of the neutral salt. Examples of the inorganic base are sodium, potassium, lithium, and so on. Examples of the organic base are various amines, such as N-methylglucamine, N,N-dimethylglucamine, ethanolamine, diethanolamine, tromethamine, 3-amino-1,2-propanediol, and morpholine, and basic amino acids, such as lysine and arginine.

The length of the alkyl chain and the number of hydroxyl groups of the straight chain or branched chain alkyl group W substituted by one or more —OH groups are not particularly limited. This alkyl group W, however, preferably has one to six carbon atoms and one to five hydroxyl groups. Preferable examples of W are a hydroxymethyl group, a 2-hydroxyethyl group, a 2,3-dihydroxypropyl group, a dihydroxyisopropyl group, and a 2,3,4-trihydroxybutyl group. Some —OH groups contained in these hydroxylalkyl groups W may be coordinate-boded to the paramagnetic metal ion Me. In addition, a sugar residual group or a hydrophilic group having a polyether structure can be used as W instead of the hydroxyalky group.

R, at least one of which is contained in Y. i.e., the substituent having one or more fluorine atoms is used to introduce $^{19}F$ as the detectable nucleus of $^{19}F$-MRI into molecules of the macro-cyclic polyamine complex compound. R is therefore not particularly limited so far as it can achieve this purpose. R is, however, preferably a straight chain or branched chain alkyl group substituted by one or more fluorine atoms. R may be of course a perfluoroalkyl group in which all hydrogen atoms are substituted by fluorine. The number of carbon atoms of these alkyl groups is preferably one to ten. Examples of such a fluorine-substituted alkyl group are a trifluoromethyl group, a perfluoroethyl group, a 2,2,2-trifluoroethyl group, a perfluoropropyl group, a bis(trifluoromethyl)methyl group, a tris(trifluoromethyl)methyl group, 2,2,3,3,3-pentafluoropropyl group, and a perfluorobutyl group. These fluorine-substituted alkyl groups may contain a functional group, such as a hydroxyl group, like a bis(trifluoromethyl)hydroxymethyl group. In addition to the above fluorine-substituted alkyl groups, an aryl group or an aralkyl group, in which one or more aromatic hydrogen atoms are substituted with fluorine atoms, can be preferably used as R. These alkyl, aryl, and aralkyl groups may contain X defined above.

The general formulas of the above preferable examples of R are as follows.

—$R^1F$;

—$R^2$—$Ar_F$, —$R_2$—Φ—$R_2$—$Ar_F$;

—$SO_2$—$R_{1F}$, —$SO_2$—$R_2$—$R_{1F}$, —$SO_2$—$Ar_F$, —$SO_2$—$R_2$—$Ar_F$; —CO—$R_{1F}$, —CO—$R_2$—$R_{1F}$, —CO—$Ar_F$, —CO—$R_2$—$Ar_F$; —$R_2$—NH—$SO_2$—$R_{1F}$, —$R_2$—NH—$SO_2$—$Ar_F$, —$R_2$—NH—$SO_2$—$R_2$—$Ar_F$; —$R_2$—$SO_2$—NH—$R_{1F}$, —$R_2$—$SO_2$—NH—$Ar_F$, —$R_2$—$SO_2$—NH—$R_2$—$Ar_F$; —$R_2$—NH—CO—$R_{1F}$, —$R_2$—NH—CO—$Ar_F$, —$R_2$—NH—CO—$R_2$—$Ar_F$; —$R_2$—CO—NH—$R_{1F}$, —$R_2$—CO—NH—$Ar_F$, —$R_2$—CO—NH—$R_2$—$Ar_F$; —$R_2$—S—$R_{1F}$, —$R_2$—S—$Ar_F$, —$R_2$—S—$R_2$—$Ar_F$; —$R_2$—O—$R_{1F}$, —$R_2$—O—$Ar_F$, —$R_2$—O—$R_2$—$Ar_F$; —$R_2$—NH—$R_{1F}$, —$R_2$—NH—$R_2$—$Ar_F$; —$R_2$—N($R_3$)—$R_{1F}$, —$R_2$—N($R_3$)—$R_2$—$Ar_F$; —$R_2$—N(X)$R_{1F}$, —$R_2$—N(X)—$R_2$—$Ar_F$; —$R_2$—N($R_{1F}$)—$R_2$—$Ar_F$, and —$R_2$—N($R_2$—$Ar_F$)$_2$, wherein X represents the same meaning as defined above, and —$R_{1F}$, —$R_2$-, —$R_3$,—Φ—, and —$Ar_F$ have the following meanings;

—$R_{1F}$: a straight chain or branched chain alkyl group which is substituted with one or more fluorine atoms and may contain X —R2—: a saturated or unsaturated hydrocarbon chain —R3: a lower alkyl group —Φ—: a phenylene group —$Ar_F$: a group represented by following the formula

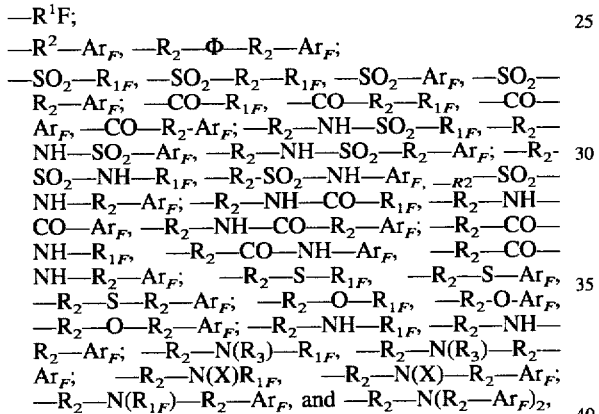

(p represents an integer from 1 to 5, and q represents 0 or an integer from 1 to 4).

The above macro-cyclic polyamine metal complex has various excellent characteristic features already described above. First, $^{19}F$ and the paramagnetic metal ion exist in the same molecule. Second, the macro-cyclic polyamine complex has a structure in which a plurality of fluorine atoms can be introduced easily into each molecule. Third, the macro-cyclic polyamine complex has a good molecular symmetry by which the chemical shifts of a plurality of fluorine atoms become essentially the same. Fourth, macro-cyclic polyamine is an extremely superior ligand, and its complex with a paramagnetic metal is very stable. Fifth, since it is easy to introduce substituents into the macro-cyclic polyamine ligand, various chemical modifications can be performed easily for the polyamine ligand.

In addition to the above characteristic features, the sixth characteristic feature of the macro-cyclic polyamine metal complex compound of the present invention is that the osmotic pressure of the entire molecule can be kept relatively low because the ligand can have a large number of hydroxyl groups at its terminal. Unlike an amino group or a carboxyl group, a hydroxyl group does not dissociate into ions in an aqueous solution. Therefore, the osmotic pressure can be kept low even if a hydroxyl group is used as a hydrophilic group. This characteristic feature makes it possible to avoid side-effects caused by a high osmotic pressure of the contrast medium when it is administered to a living body.

The macro-cyclic polyamine metal complex compound of the present invention can be manufactured easily by using materials including commercially available macro-cyclic polyamine, through reactions well known to those skilled in the art in accordance with synthesis routes described below.

Synthesis route:

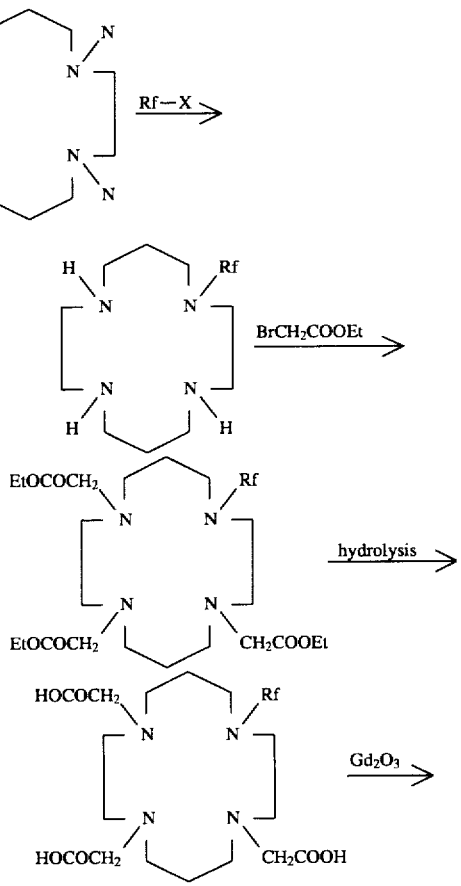

-continued
Synthesis route:

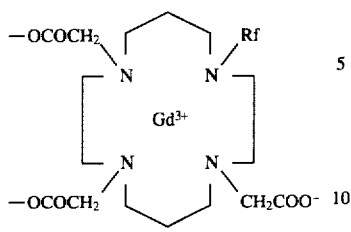

Rf: fluoroalkyl

The final compound synthesized by the above routes can be isolated and purified by regular methods used in organic syntheses, such as an ion exchanging treatment, an activated carbon treatment, solvent precipitation, evaporation to dryness, recrystallization, and spray drying.

In order to obtain the final product in the form of various salts or in order to match the final product to the pH of a living body, an equivalent amount of counter ions may be added to a free compound to cause a reaction, and then the compound need only be isolated and purified in the same manner as described above.

The present invention will be described in more detail below by way of its examples, but these examples are presented merely for the purpose of illustrating the present invention, so it is to be understood that the present invention is not limited to these examples.

EXAMPLE 1

Synthesis of gadolinium complex with
1-(2,2,2-trifluoroethyl)-1,4,8,11-
tetraazacyclodecane-4,8,11-tetraacetic acid
(compound 1, formula IV)

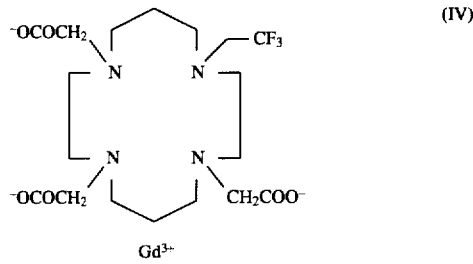

(IV)

[Reaction 1] 1,4,8,11-Tetraazacyclotetradecane (20 g, 100 mmol) and 2,2,2-trifluoroethylbromide (16 g, 100 mmol) were dissolved in 400 ml of chloroform. After stirring for 5 hrs. at room temperature, the reaction mixture was evaporated under reduced pressure. The residue was purified through silica gel column chromatography eluted by mixed solvent (aqueous ammonia solution: methanol=1:9). The yield was 53%.

[Reaction 2] To a solution of the product of Reaction 1 (15 g, 53 mmol) in dimethylformamide 100 ml), triethylamine (125 ml, 900 mmol) was added followed by adding dropwise 150 g (900 mmol) of bromoethylacetate. After stirring for 2 hrs. at 70° C., the reaction mixture was evaporated under reduced pressure. The residue was purified through silica gel column chromatography eluted by mixed solvent of methanol/chloroform=1/9. The yield was 80%.

[Reaction 3] A solution of the product of Reaction 2 (23 g, 42 mmol) in 50 ml of methanol was added with 127 ml of 1N sodium hydroxide aqueous solution and stirred at room temperature for 12 hrs. The reaction mixture was evaporated to be concentrated under reduced pressure, and then, the concentrate was treated by cation exchange resin (Amberlite IR-120B) to remove sodium cation. The yield was 90%.

The physio-chemical data of the obtained ligand compound were analyzed. Note that the spectral data were measured under following conditions.
<NMR analysis>
Apparatus: EX-90 manufactured by Nihon Denshi K.K.(90 MHz)
Solvent: Heavy water or Dimethylsulfoxide-d 6
Standard substances: DSS($^1$H), Trifluoroacetic acid($^{19}$F)
<IR analysis>
Apparatus: IR-810 manufactured by Nihon Bunko K.K.
Method: KBr tablet method
<MS analysis>
Apparatus: D-300 manufactured by Nihon Denshi K.K.
Method: FAB ionizing method (glycerin matrix containing hydrochloric acid)
Analytical Data of the ligand compound were as follows;
Molecular formula: $C_{18}H_{31}N_4O_6F_3$
$^1$H-NMR (δppm): 2.3 (m, CCH$_2$C), 2.8 (m, CH$_2$N), 3.2 (m, CH$_2$CF$_3$), 3.5 (s, CH$_2$CO)
$^{19}$F-NMR (δppm): −68.1
IR (vcm$^{-1}$): 2600–3400, 1720–1760 (COOH), 1240 (CF$_3$)
FAB-MS (M/Z): 457 (MH$^+$)

[Reaction 4 (Synthesis of complex)] The product of Reaction 3 (10 g, 22 mmol) were dissolved in 100 ml of distilled water containing 33 ml of 1N sodium hydroxide, and gadolinium oxide (4.0 g, 11 mmol) were added. The solution was stirred under heating at 80° C. for 6 hrs. The reaction mixture was filtered for removal of unreacted gadolinium oxide, and the clear filtrate was evaporated to dryness under reduced pressure. The residue was dissolved in a small amount of water and treated by a cation exchange resin (Amberlite IR-120B) and dried to solid under reduced pressure. The yield was 90%.

Note that the yield of complexation reaction was calculated from the weight and the metal quantity determined by ICP (Inductively Coupled Plasma emission spectroscopy). The yield was 90% and 12.8 g of the end product were obtained. The overall yield was 32%.

EXAMPLE 2

Synthesis of gadolinium complex of
1-(1-carboxy-3,3,3-trifluoropropyl)-1,4,8,11-
tetraazacyclotetradecane-4,8,11-triacetic acid
(compound 2, formula V)

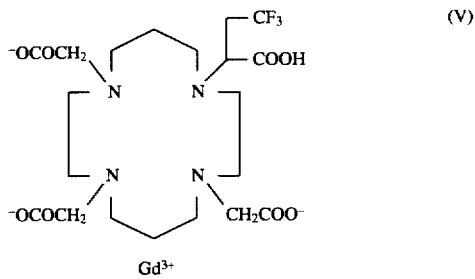

(V)

[Reaction 1] 1,4,8,11-Tetraazacyclotetradecane (20 g, 100 mmol) and 2-iodo-4,4,4-trifluorobutyric acid (27 g, 100 mmol) were dissolved in 200ml of chloroform. After stirring for 5 hrs. at room temperature, the reaction mixture was evaporated under reduced pressure. The residue was purified through silica gel column chromatography eluted by ammonia aqueous solution/methanol=1/9. The yield was 56%.

[Reaction 2] The reaction was performed in the same procedure as described in Reaction 2 of Example 1 except that the product of Reaction 1 was used as a starting material. The yield was 83%.

[Reaction 3] The reaction was performed in the same procedure as described in Reaction 3 of Example 1 except that the product of Reaction 2 was used as a starting material. The yield was 86%.

<Analytical Data>

Molecular formula: $C_{20}H_{33}N_4O_8F_3$ $^1$H-NMR (δppm): 1.9(m,CCH$_2$CF$_3$), 2.3(m,CCH$_2$C), 3.0(m,CH$_2$N), 3.3(s,CH$_2$CO), 3.4(s,CH$_2$CO), 3.6(m,CH)

$^{19}$F-NMR (δppm): −65.4

IR (vcm$^{-1}$): 2600–3400, 1720–1760 (COOH), 1260 (CF$_3$)

FAB-MS (M/Z): 515 (MH$^+$)

[Reaction 4 (Synthesis of complex)] The reaction was performed in the same procedure as described in Reaction 4 of Example 1 except that the product of Reaction 3 was used as a starting material. The yield was 89% and 12.2 g of the end product were obtained. The overall yield was 36%.

EXAMPLE 3

Synthesis of gadolinium complex of 1-[4-trifluoromethyl)benzyl]-1,4,8,11-Tetraazacyclotetradecane-4,8,11-triacetic acid (compound 3, formula VI)

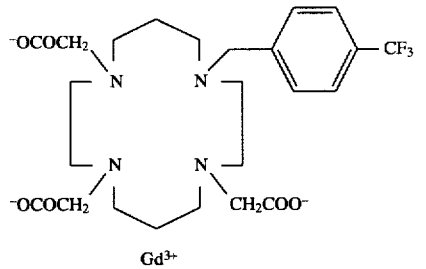

(VI)

[Reaction 1] 1,4,8,11-Tetraazacyclotetradecane (20 g, 100 mmol) and 4-trifluoromethylbenzyl bromide (24 g, 100 mmol) were dissolved in 200 ml of chloroform. After 5hr-stirring at room temperature, the reaction mixture was evaporated under reduced pressure. The residue was purified through silica gel column chromatography eluted by ammonia aqueous solution/methanol=1/9. The yield was 63%.

[Reaction 2] The reaction was performed in the same procedure as described in Reaction 2 of Example 1 except that the product of Reaction 1 was used as a starting material. The yield was 79%.

[Reaction 3] The reaction was performed in the same procedure as described in Reaction 3 of Example 1 except that the product of Reaction 2 was used as a starting material. The yield was 82%.

<Analytical Data>

Molecular formula: $C_{24}H_{35}N_4O_6F_3$ $^1$H-NMR (δppm): 2.3(m,CCH$_2$C), 2.7(m,CH$_2$N), 3.2(s, CH$_2$CO), 3.3(s,CH$_2$CO), 3.7(s,Φ—CH$_2$), 7.4–7.8(m,Φ)

$^{19}$F-NMR (δppm): −65.1

IR (vcm$^{-1}$): 2600–3400, 1720–1760(COOH), 1240(CF$_3$)

FAB-MS (M/Z): 533 (MH$^+$)

[Reaction 4 (Synthesis of complex)] The reaction was performed in the same procedure as described in Reaction 4 of Example 1 except that the product of Reaction 3 was used as a starting material. The yield was 92% and 12.5 g of the end product were obtained. The overall yield was 38%.

EXAMPLE 4

Synthesis of gadolinium complex of 1-[3,5-bis(trifluoromethyl)benzyl]-,1,4,8,11-tetraazacyclotetradecane-4,8,11-triacetic acid (compound 4, formula VII)

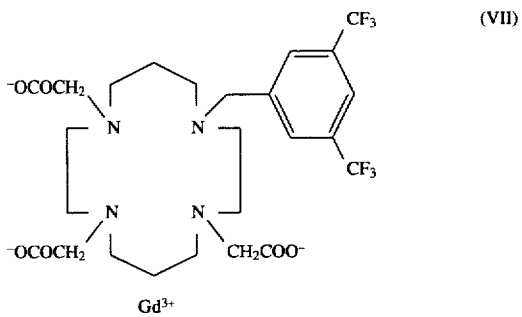

(VII)

[Reaction 1] 1,4,8,11-Tetraazacyclotetradecane (20 g, 100 mmol) and 3,5-bis(trifluoromethyl)benzyl bromide (31 g, 100 mmol) were dissolved in 200 ml of chloroform. After 5hr-stirring at room temperature, the reaction mixture was evaporated under reduced pressure. The residue was purified through silica gel column chromatography eluted by ammonia aqueous solution/methanol=1/9. The yield was 57%.

[Reaction 2] The reaction was performed in the same procedure as described in Reaction 2 of Example 1 except that the product of Reaction 1 was used as a starting material. The yield was 84%.

[Reaction 3] The reaction was performed in the same procedure as described in Reaction 3 of Example 1 except that the product of Reaction 2 was used as a starting material. The yield was 86%.

<Analytical Data>

Molecular formula: $C_{25}H_{34}N_4O_6F_6$ $^1$H-NMR (δppm): 2.3(m,CCH$_2$C), 2.6(m,CH$_2$N), 3.5(s, CH$_2$CO), 3.6(s,CH$_2$CO), 3.7(s,Φ—CH$_2$), 7.9–8.2(m,Φ)

$^{19}$F-NMR (δppm): −65.2

IR (vcm$^{-1}$): 2600–3400, 1720–1760(COOH), 1240(CF$_3$)

FAB-MS (M/Z): 601 (MH$^+$)

[Reaction 4 (Synthesis of complex)] The reaction was performed in the same procedure as described in Reaction of Example 1 except that the product of Reaction 3 was used as a starting material. The yield was 94% and 12.4 g of the end product were obtained. The overall yield was 39%.

EXAMPLE 5

The gadolinium complex of 1,8-bis[3,5-bis(trifluoromethyl)benzyl]-1,4,8,11-tetraazacyclododecane-4,11-diacetic acid (compound 5, formula VIII)

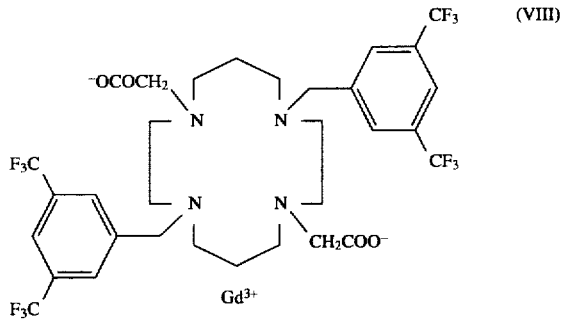

(VIII)

17

[Reaction 1] The reaction was performed in the same procedure as described in Reaction 1 of Example 4 except that the amount of 3,5-bis(trifluoromethyl) benzyl bromide used as a reagent were 62 g (200 mmol). The yield was 38%.

[Reaction 2] The reaction was performed in the same procedure as described in Reaction 2 of Example 4 except that the amount of bromoethylacetate used as a reagent were 80 g (200 mmol). The yield was 95%.

[Reaction 3] The reaction was performed in the same procedure as described in Reaction 3 of Example 4 except that the amount of 1N sodium hydroxide used as a reagent were 72 ml. The yield was 88%.

<Analytical Data>

Molecular formula: $C_{32}H_{36}N_4O_4F_{12}$
$^1$H-NMR (δppm): 2.4(m,$\ddot{C}CH_2\ddot{C}$), 2.6(m,$CH_2$N), 3.5(s, $CH_2CO$), 3.7(s,$CH_2CO$), 3.7(s,Φ—$CH_2$), 7.9–8.2(m,Φ)
$^{19}$F-NMR (δppm): –65.1
IR (vcm$^{-1}$): 2600–3400, 1720–1760(COOH), 1250(CF$_3$)
FAB-MS (M/Z): 769 (MH$^+$)

[Reaction 4 (Synthesis of complex)] The reaction was performed in the same procedure as described in Reaction 4 of Example 4 except that the product of Reaction 3 was used as a starting material and 100 ml of distilled water containing 13 ml of 1N sodium hydroxide used as a solvent. The yield was 97% and 10.1 g of the end product were obtained. The overall yield was 31%.

EXAMPLE 6

Synthesis of gadolinium complex of 1,4,8-Tris[3,5-bis(trifluoromethyl)benzyl]-1,4,8,11-tetraazacyclotetradecane-11-acetic acid (compound 6, formula IX)

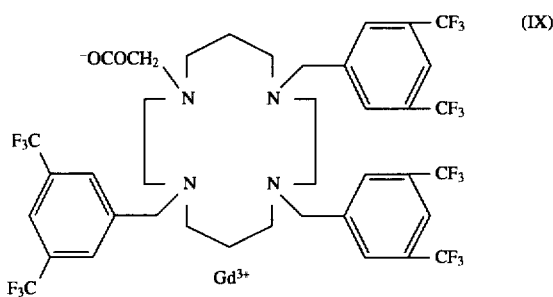

[Reaction 1] The reaction was performed in the same procedure as described in Reaction 1 of Example 4 except that the amount of 3,5-bis(trifluoromethyl) benzyl bromide used as a reagent were 93 g (300 mmol). The yield was 42%.

[Reaction 2] The reaction was performed in the same procedure as described in Reaction 2 of Example 4 except that the amount of bromoethylacetate used as a reagent were 40 g (100 mmol). The yield was 93%.

[Reaction 3] The reaction was performed in the same procedure as described in Reaction 3 of Example 4 except that the amount of 1N sodium hydroxide used as a reagent were 39 ml. The yield was 83%.

<Analytical Data>

Molecular formula: $C_{39}H_{38}N_4O_2F18$
1H-NMR (δppm): 2.2(m,$\ddot{C}CH_2\ddot{C}$), 2.6(m,$CH_2$N), 3.5(s, $CH_2CO$), 3.7(s,$CH_2CO$), 3.7(s,Φ—$CH_2$), 7.9–8.2(m,Φ)
$^{19}$F-NMR (δppm): –65.2
IR (vcm$^{-1}$): 2600–3400, 1720–1760(COOH), 1250(CF$_3$)
FAB-MS (M/Z): 937 (MH$^+$)

[Reaction 4 (Synthesis of complex)] The reaction was performed in the same procedure as described in Reaction of Example 4 except that the product of Reaction 3 was used as a starting material and 100 ml of distilled water containing 5 ml of 1N sodium hydroxide used as a solvent. The yield was 94% and 11.1 g of the end product were obtained. The overall yield was 30%.

EXAMPLE 7

Synthesis of gadolinium complex of 1,4,8,11-Tetrakis[3,5-bis(trifluoromethyl)benzyl]-1,4,8,11-tetraazacyclotetradecane (compound 7, formula X)

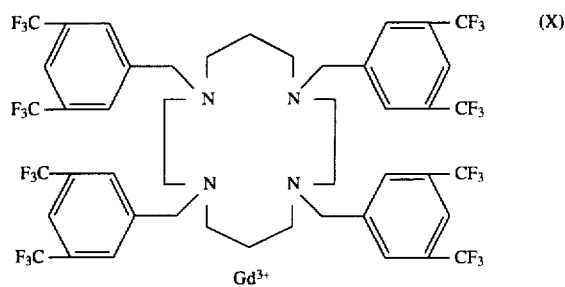

[Reaction 1] The reaction was performed in the same procedure as described in Reaction 1 of Example 4 except that the amount of 3,5-bis(trifluoromethyl) benzyl bromide used as a reagent were 124 g (400 mmol). The yield was 52%.

<Analytical Data>

Molecular formula: $C_{46}H_{40}N_4F_{24}$
$^1$H-NMR (δppm): 2.2(m,$\ddot{C}CH_2\ddot{C}$), 2.6(m,$CH_2$N), 3.7(s,Φ—$CH_2$), 7.9–8.2(m,Φ)
$^{19}$F-NMR (δppm): –65.3
IR (vcm$^{-1}$): 1250(CF$_3$)
FAB-MS (M/Z): 1105 (MH$^+$)

[Reaction 2 (Synthesis of complex)] The product of Reaction 1 (10 g, 9 mmol) were dissolved in 100 ml of distilled water containing 50 ml methanol, and gadolinium oxide (4.0 g, 11 mmol) were added. The solution was stirred under heating at 50° C. for 15 hrs. The reaction mixture was filtered for removal of unreacted gadolinium oxide, and the clear filtrate was evaporated to dryness under reduced pressure. The residue was dissolved small amount of water and treated by a cation exchange resin (Amberlite IR-120B) and dried to solid under reduced pressure. The yield was 86% and 9.8 g of the end product were obtained. The overall yield was 45%.

EXAMPLE 8

Synthesis of gadolinium complex of 1-[3,5-bis(trifluoromethyl)benzyl]1,4,7,10-tetraazacyclododecane-4,7,10-triacetic acid (compound 8, formula XI)

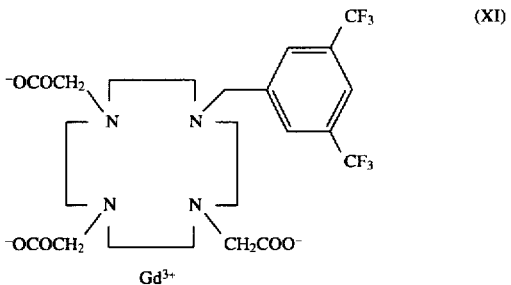

[Reaction 1] 1,4,7,10-Tetraazacyclotetradecane (17 g, 100 mmol) and 3,5-bis(trifluoromethyl)benzyl bromide (31 g, 100 mmol) were dissolved in 200 ml of chloroform. After 5hr-stirring at room temperature, the reaction mixture was evaporated under reduced pressure. The residue was purified through silica gel column chromatography eluted by ammonia aqueous solution/methanol=1/9. The yield was 64%.

[Reaction 2] The reaction was performed in the same procedure as described in Reaction 2 of Example 1 except that the product of Reaction 1 was used as a starting material. The yield was 81%.

[Reaction 3] The reaction was performed in the same procedure as described in Reaction 3 of Example 1 except that the product of Reaction 2 was used as a starting material. The yield was 83%.

<Analytical Data>

Molecular formula: $C_{23}H_{30}N_4O_6F_6$ $^1$H-NMR (δppm): 2.6(m,$CH_2$N), 3.5(s,$CH_2$CO), 3.7(s, Φ—$CH_2$), 7.9–8.2(m,Φ)

$^{19}$F-NMR (δppm): –65.2

IR (vcm$^{-1}$): 2600–3400, 1720–1760(COOH), 1250($CF_3$)

FAB-MS (M/Z): 573 (MH$^+$)

[Reaction 4 (Synthesis of complex)] The reaction was performed in the same procedure as described in Reaction 4 of Example 1 except that the product of Reaction 3 was used as a starting material. The yield was 96% and 2.8 g of the end product were obtained. The overall yield was 41%.

EXAMPLE 9

Synthesis of gadolinium complex of

1-[3,5-bis(trifluoromethyl)benzyl]-1,4,8,11-tetraazacyclododecane-5,7-dion-4,8,11-triacetic acid (compound 9, formula XII)

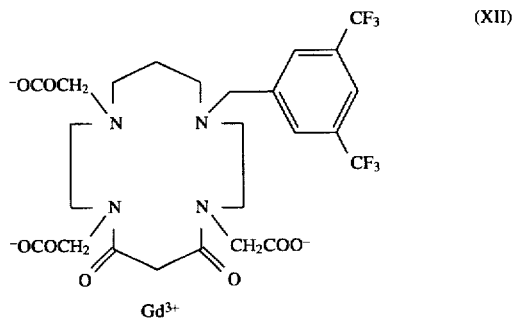

[Reaction 1] 1,4,8,11-Tetraazacyclotetradecane-5,7-dion (23 g, 100 mmol) and 3,5-bis(trifluoromethyl)benzyl bromide (31 g,100 mmol) were dissolved in 200 ml of chloroform. After 5hr-stirring at room temperature, the reaction mixture was evaporated under reduced pressure. The residue was purified through silica gel column chromatography eluted by ammonia aqueous solution/methanol=1/9. The yield was 64%.

[Reaction 2] The reaction was performed in the same procedure as described in Reaction 2 of Example 1 except that the product of Reaction 1 was used as a starting material. The yield was 75%.

[Reaction 3] The reaction was performed in the same procedure as described in Reaction 3 of Example 1 except that the product of Reaction 2 was used as a starting material. The yield was 82%.

<Analytical Data>

Molecular formula: $C_{25}H_{30}N_4O_8F_6$ $^1$H-NMR (δppm): 2.6–3.0(m,$CH_2$N), 3.2(s,$CH_2$), 3.6($CH_2$CO), 3.7(s, Φ—$CH_2$), 7.9–8.2(m,Φ)

$^{19}$F-NMR (δppm): –65.0

IR (vcm$^{-1}$): 2600–3400, 1720–1760(COOH,CO), 1250($CF_3$)

FAB-MS (M/Z): 629 (MH$^+$)

[Reaction 4 (Synthesis of complex)] The reaction was performed in the same procedure as described in Reaction 4 of Example 1 except that the product of Reaction 3 was used as a starting material. The yield was 91% and 11.9 g of the end product were obtained. The overall yield was 41%.

EXAMPLE 10

Synthesis of gadolinium complex of

1-[4-[tris(trifluoromethyl)methyl]benzyl]-1,4,8,11-tetraazacyclotetradecane-4,8,11-triacetic acid (compound 10, formula XIII)

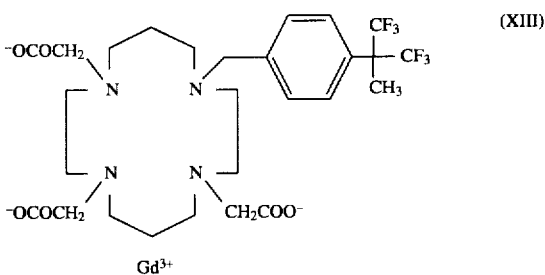

[Reaction 1] 1,4,8,11-Tetraazacyclotetradecane (20 g, 100 mmol) and 4-[tris(trifluoromethyl)]benzyl bromide (39 g, 100 mmol) were dissolved in 200 ml of chloroform. After 5hr-stirring at room temperature, the reaction mixture was evaporated under reduced pressure. The residue was purified through silica gel column chromatography eluted by ammonia aqueous solution/methanol=1/9. The yield was 54%.

[Reaction 2] The reaction was performed in the same procedure as described in Reaction 2 of Example 1 except that the product of Reaction 1 was used as a starting material. The yield was 81%.

[Reaction 3] The reaction was performed in the same procedure as described in Reaction 3 of Example 1 except that the product of Reaction 2 was used as a starting material. The yield was 87%.

<Analytical Data>

Molecular formula: $C_{27}H_{35}N_4O_6F_9$ $^1$H-NMR (δppm): 2.3(m,C$CH_2$C), 2.8(m,$CH_2$N), 3.3(s, $CH_2$CO), 3.6(s,$CH_2$CO), 3.7(s,Φ—$CH_2$), 7.9–8.2(m,Φ) $^{19}$F-NMR (δppm): –63.8

IR (vcm$^{-1}$): 2600–3400, 1720–1760(COOH), 1240($CF_3$)

FAB-MS (M/Z):683 (MH$^+$)

[Reaction 4 (Synthesis of complex)] The reaction was performed in the same procedure as described in Reaction of Example 1 except that the product of Reaction 3 was used as a starting material. The yield was 96% and 12.3 g of the end product were obtained. The overall yield was 37%.

EXAMPLE 11

Synthesis of gadolinium complex of 1-(pentafluorobenzyl)-1,4,8,11-tetraazacyclotetradecane-4,8,11-triacetic acid (compound 11, formula XIV)

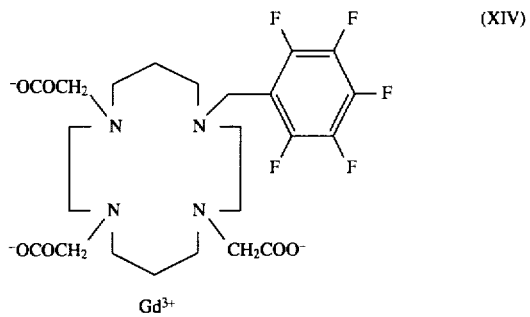

[Reaction 1] 1,4,8,11-Tetraazacyclotetradecane (20 g, 100 mmol) and 2,3,4,5,6-pentafluorobenzyl bromide (26 g, 100 mmol) were dissolved in 200 ml of chloroform. After 5hr-stirring at room temperature, the reaction mixture was evaporated under reduced pressure. The residue was purified through silica gel column chromatography eluted by ammonia aqueous solution/methanol=1/9. The yield was 50%.

[Reaction 2] The reaction was performed in the same procedure as described in Reaction 2 of Example 1 except that the product of Reaction 1 was used as a starting material. The yield was 78%.

[Reaction 3] The reaction was performed in the same procedure as described in Reaction 3 of Example 1 except that the product of Reaction 2 was used as a starting material. The yield was 91%.

<Analytical Data>
Molecular formula: $C_{23}H_{31}N_4O_6F_5$
$^1$H-NMR (δppm): 2.3(m,$CCH_2C$), 2.7(m,$CH_2N$), 3.1(s, $CH_2CO$), 3.6(s, Φ—$CH_2$)
$^{19}$F-NMR (δppm): −160 to −150
IR (vcm$^{-1}$): 2600–3400, 1720–1760(COOH)
FAB-MS (M/Z): 555 (MH$^+$)

[Reaction 4 (Synthesis of complex)] The reaction was performed in the same procedure as described in Reaction 4 of Example 1 except that the product of Reaction 3 was used as a starting material. The yield was 92% and 12.4 g of the end product were obtained. The overall yield was 33%.

EXAMPLE 12

Synthesis of gadolinium complex of 1-[3,5-bis(trifluoromethyl)benzyl]-1,4,8,11-tetraazacyclotetradecane-4,8,11-triacetic acid-tris(2,3-dihydroxyamide) (compound 12, formula XV)

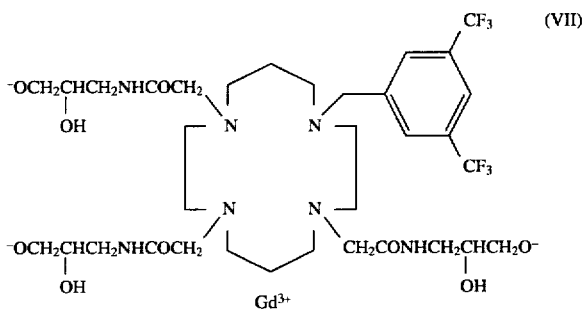

[Reaction 1] 28 g (41 mmol) of the product of Reaction 3 in Example 5 in Reaction 3 was mixed with 27 g (186 mmol) of 2,3-dihydroxy-n-propylamine. The mixture was stirred at 100° C. under heating for 2 hrs. The reaction mixture was dissolved in small amount water and placed in short column filled by cation exchange resin (Amberlite IR-120B). The fraction containing product was collected and evaporated to dryness under reduced pressure. The yield was 76%.

<Analytical Data>
Molecular formula: $C_{34}H_{55}N_7O_9F_6$
$^1$H-NMR (δppm): 2.3(m,$CCH_2C$), 2.9(m,$CH_2N$), 3.7(s, Φ—$CH_2$), 3.6–4.2(m,amide side chain), 7.6–7.9(m,Φ)
$^{19}$F-NMR (δppm):
−64.8
IR (vcm$^{-1}$): 3200–3600(OH), 1650(CONH), 1290($CF_3$)
FAB-MS (M/Z): 820 (MH$^+$)

[Reaction 2 (Synthesis of complex)] The reaction was performed in the same procedure as described in Reaction of Example 1 except that the product of Reaction 1 was used as a starting material. The yield was 90% and 10.7 g of the end product were obtained. The overall yield was 29%.

EXAMPLE 13

Synthesis of gadolinium complex of 1-[4-[2-trans-(3,5-bis(trifluoromethyl)phenyl)vinyl]benzyl]-1,4,8,11-tetraazacyclotetradecane-4,8,11-triacetic acid (compound 13, formula XVI)

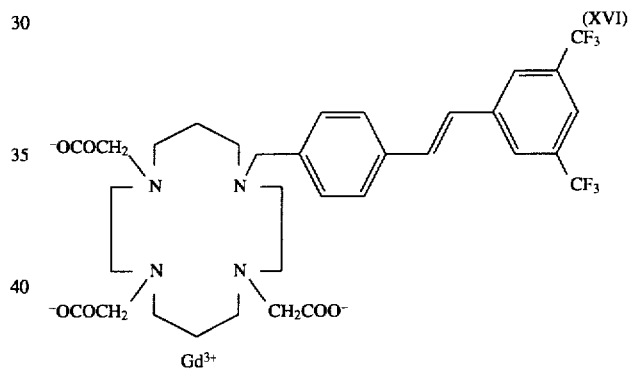

[Reaction 1] To a solution of 4-methylbenzyl bromide (500 g, 270 mmol) in dried tetrahydrofuran (300 ml) was added 71 g (270 mmol) of triphenylphosphine and the mixture was refluxed for 1 hr. After cooling to room temperature, a precipitate was collected by filtration and washed small amount of tetrahydrofuran. The product was dried under reduced pressure, gave a white solid by 85% yield.

[Reaction 2] To a solution of the product of Reaction 1 (103 g, 230 mmol) in methanol (350 ml), 52 ml (270 mmol) of 28% sodium methoxide in methanol solution was added. Subsequently, 56 g (270 m mol) of 3,5-bis(tri-fluoromethyl)benzyl bromide was added drop-wise into the reaction mixture at 0° C, and stirred for 2 hrs. at room temperature. The reaction mixture was evaporated, and added with 100 ml of ethylacetate. Then solution was washed with water and saturated brine twice, dried over anhydrous sodiumsulfate, and purified through silica gel column chromatography eluted by ethylacetate/n-hexane=1/19. The yield was 60%.

[Reaction 3] To a solution of the product of Reaction 2 (46 g, 138 mmol), 37 g (105 mmol) of N-Bromosuccinimide was added and the mixture was then refluxed for 3 hrs. The reaction mixture was filtered and the filtrate was evaporated. The residue was purified through silica gel chromatography eluted by ethylacetate/n-Hexane=1/19. The yield was 75%.

23

[Reaction 4] To a solution of 1,4,8,11-Tetraazacyclotetradecane (21 g, 124 mmol) and Triethylamine (13 g, 124 mmol) in dried tetrahydrofuran, 40 g (103 mmol) of the product of Reaction 3 was added dropwise at 0° C. and stirred for 3 hrs. at room temperature. The reaction mixture was poured into water and extracted with ethylacetate. The organic layer was washed by saturated brine, dried over anhydrous sodiumsulfate, and evaporated under reduced pressure. The residue was purified through silica gel column chromatography eluted by ethylacetate/n-Hexane=3/7. The yield was 80%.

[Reaction 5] The reaction was performed in the same procedure as described in Reaction 2 of Example 1 except that the product of Reaction 4 was used as a starting material. The yield was 82%.

[Reaction 6] The reaction was performed in the same procedure as described in Reaction 3 of Example 1 except that the product of Reaction 5 was used as a starting material. The yield was 89%.

<Analytical Data>

Molecular formula: $C_{33}H_{40}N_4O_6F_6$ $^1$H-NMR (δppm): 2.3(m,CCH$_2$C), 2.8(m,CH$_2$N), 3.4(s, CH$_2$CO), 3.6 (m,CH$_2$ ), 6.8–7.3 (m,CH=CH), 7.1–7.8(m, Φ)

$^{19}$F-NMR (δppm): –68.1

IR (vcm$^{-1}$): 2600–3400, 1730–1770(COOH), 1270(CF$_3$)

FAB-MS (M/Z): 703 (MH$^+$)

[Reaction 7 (Synthesis of complex)] The reaction was performed in the same procedure as described in Reaction 4 of Example 1 except that the product of Reaction 6 was used as a starting material. The yield was 97% and 12.3 g of the end product were obtained. The overall yield was 22%.

EXAMPLE 14

Synthesis of gadolinium complex of 1-[3,5-bis(trifluoromethyl)benzenesulfonyl]-1, 4,8,11-tetraazacyclotetradecane-4,8,11-triacetic acid (compound 14, formula XVII)

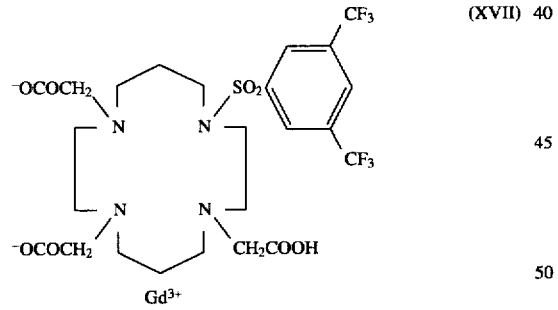

[Reaction 1] To solution containing 1,4,8,11-Tetraazacyclotetradecane (16 g, 95 mmol) and pottasiumbicarbonate (66 g, 48 mmol) in 300 ml of distilled water, 3,5-bis(trifluoromethyl)benzene-sulfonyl chloride (25 g, 80 mmol) in tetrahydrofuran was added dropwise under cooling over 30 min., and the resultant solution was stirred at room temperature for 5 hrs. After standing several minutes, the organic layer was separated and remained aqueous layer was extracted with 200 ml of ether twice. The extract and the organic layer from reaction mixture were combined, wash with saturated brine, dried over anhydrous sodiumsulfate, and evaporated to dryness under reduced pressure. The yield was 89%.

[Reaction 2] The reaction was performed in the same procedure as described in Reaction 2 of Example 1 except

24 that the product of Reaction 1 was used as a starting material. The yield was 84%.

[Reaction 3] The reaction was performed in the same procedure as described in Reaction 3 of Example 1 except that the product of Reaction 2 was used as a starting material. The yield was 89%.

<Analytical Data>

Molecular formula: $C_{24}H_{32}N_4O_8F_6S$ $^1$H-NMR (δppm): 2.3(m,CCH$_2$C), 2.8(m,CH$_2$N), 3.7(s, CH$_2$CO), 3.8(s,CH$_2$CO), 7.9–8.2(m,Φ)

$^{19}$F-NMR (δppm): –63.8

IR (vcm$^{-1}$): 2600–3400, 1720–1760(COOH), 1350(SO$_2$N), 1240(CF$_3$)

FAB-MS (M/Z): 651 (MH$^+$)

[Reaction 4 (Synthesis of complex)] The reaction was performed in the same procedure as described in Reaction 4 of Example 1 except that the product of Reaction 3 was used as a starting material. The yield was 97% and 12.5 g of the end product were obtained. The overall yield was 65%.

EXAMPLE 15

Synthesis of gadolinium complex of 1-[3,5-bis(trifluoromethyl)benzene carbonyl]-1,4,8,11-tetraazacyclotetradecane-4,8,11-triacetic acid (compound 15, formula XVIII)

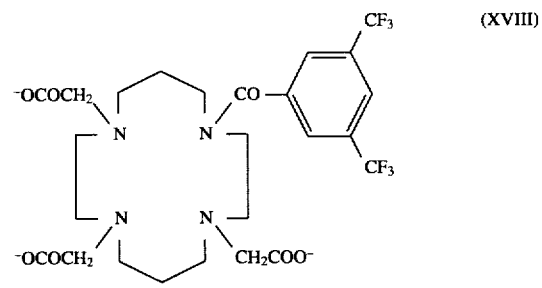

[Reaction 1] To a solution containing 1,4,8,11-tetraazacyclotetradecane (16 g, 95 mmol) and pottasiumbicarbonate (66 g, 48 mmol) in 300 ml of distilled water, 3,5-bis(trifluoromethyl)benzoyl chloride (22 g, 80 mmol) in tetrahydrofuran was added dropwise under cooling over 30 min., and the resultant mixture was stirred at room temperature for 5 hrs. The mixture was treated in the same manner as described in Reaction 1 of Example 14. The yield was 81%.

[Reaction 2] The reaction was performed in the same procedure as described in Reaction 2 of Example 1 except that the product of Reaction 1 was used as a starting material. The yield was 87%.

[Reaction 3] The reaction was performed in the same procedure as described in Reaction 3 of Example 1 except that the product of Reaction 2 was used as a starting material. The yield was 88%.

<Analytical Data>

Molecular formula: $C_{25}H_{32}N_4O_7F_6$ $^1$H-NMR (δppm): 2.3(m,CCH$_2$C), 2.9(m,CH$_2$N), 3.7(s, CH$_2$CO), 3.8(s,CH$_2$CO), 7.9–8.2(m,Φ)

$^{19}$F-NMR (δppm): –64.9

IR (vcm$^{-1}$): 2600–3400, 1720–1760(COOH, CONH), 1260(CF$_3$)

FAB-MS (M/Z): 615 (MH$^+$)

[Reaction 4 (Synthesis of complex)] The reaction was performed in the same procedure as described in Reaction 4 of Example 1 except that the product of Reaction 3 was used as a starting material. The yield was 95% and 12.4 g of the end product were obtained. The overall yield was 59%.

EXAMPLE 16

Synthesis of gadolinium complex of 1-[2-[3,5-bis(trifluoromethyl) phenylsulfonylamino]ethyl]-1,4,8,11-tetraazacyclotetradecane-4,8,11-triacetic acid (compound 16, formula XIX)

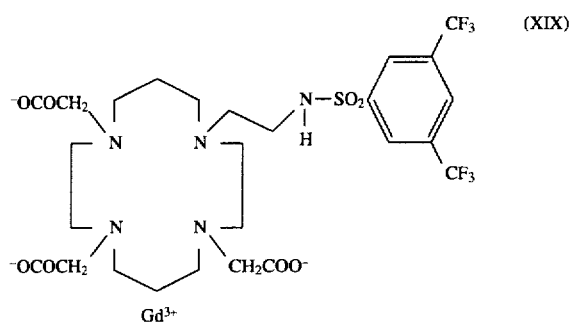

[Reaction 1] To a solution of monoethanolamine (18 g, 300 mmol) in 300 ml of tetrahydrofuran, sodium bicarbonate (21 g, 200 mmol) in 200 ml of water was added, followed by addition of 3,5-bis(trifluoromethyl) sulfonyl chloride (63 g, 200 mmol). After stirring at room temperature for 15 hrs., 200 ml of ethylacetate was added to the reaction mixture. The separated organic layer was washed twice with water and once with saturated brine, dried over anhydrous sodiumsulfate, and evaporated under reduced pressure. The yield was 87%.

[Reaction 2] The product of Reaction 1 (57 g, 174 mmol) was dissolved in 100ml of dried pyridine. Recrystallized p-toluenesulfonylchloride (40 g, 210 mmol) was added under cooling by ice bath over 1 hr. and the mixture was stirred at room temperature for 1 hr. The reaction mixture was poured into ice-water and extracted with 200 ml ethylacetate. The organic layer was washed twice with diluted hydrochloric acid, twice with distilled water, and once with saturated brine. The resultant solution was dried over anhydrous sodiumsulfate and evaporated to dryness under reduced pressure. The yield was 71%.

[Reaction 3] To a solution of 1,4,8,11-tetraazacyclotetradecane(21 g, 124 mmol) in 100ml of dried dimethyl formamide, pottasiumbicarbonate (20 g, 148 mmol) was added, followed by addition of the product of Reaction 2 (59 g, 123 mmol). After stirring at 70° C. for 5 hrs., the reaction mixture was evaporated to concentrate. The residue was diluted with distilled water and extracted with ethylacetate. The organic layer was washed with distilled water and saturated brine, and dried over anhydrous sodiumsulfate. The extract was evaporated and the residue was purified by silica gel column chromatography eluted with ethylacetate/n-hexan=3/7. The yield was 77%.

[Reaction 4] The reaction was performed in the same procedure as described in Reaction 2 of Example 1 except that the product of Reaction 3 was used as a starting material. The yield was 73%.

[Reaction 5] The reaction was performed in the same procedure as described in Reaction 3 of Example 1 except that the product of Reaction 4 was used as a starting material. The yield was 92%.
<Analytical Data>

Molecular formula: $C_{26}H_{37}N_8O_6F_6S$
$^1$H-NMR (δppm): 2.3(m,CCH$_2$C), 2.8(m,CH$_2$N), 3.5(s, CH$_2$CO), 3.6(s,CH$_2$CO), 7.7-7.8(m,Φ)
$^{19}$F-NMR (δppm): -68.3
IR (vcm$^{-1}$): 2620-3410, 1730-1760(COOH), 1280(CF$_3$)
FAB-MS (M/Z): 694 (MH$^+$)

[Reaction 6 (Synthesis of complex)] The reaction was performed in the same procedure as described in Reaction 4 of Example 1 except that the product of Reaction 5 was used as a starting material. The yield was 98% and 12.5 g of the end product were obtained. The overall yield was 31%.

EXAMPLE 17

Synthesis of gadolinium complex of 1-[2-[3,5-bis(trifluoromethyl) phenylcarbonylamino]ethyl]-1,4,8,11-tetraazacyclotetradecane-4,8,11-triacetic acid (compound 17, formula XX)

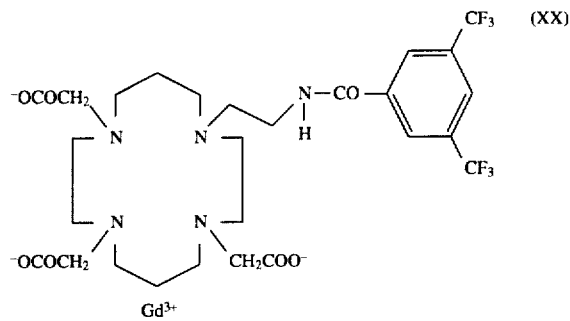

[Reaction 1] To a solution of monoethanolamine (18 g, 300 mmol) in 300 ml of tetrahydrofuran, sodium bicarbonate (21 g, 200 retool) in 200 ml of water was added, followed by addition of 3,5- bis(trifluoromethyl)benzoyl chloride(63 g, 200 mmol). After stirring at room temperature for 20 hrs., 200 ml of ethylacetate was added to the reaction mixture. The separated organic layer was washed twice with water and once with saturated brine, dried over anhydrous sodiumsulfate, and evaporated under reduced pressure. The yield was 87%.

[Reaction 2] The reaction was performed in the same procedure as described in Reaction 2 of Example 16 except that the product of Reaction 1 was used as a starting material. The yield was 72%.

[Reaction 3] The reaction was performed in the same procedure as described in Reaction 3 of Example 16 except that the product of Reaction 2 was used as a starting material. The yield was 76%.

[Reaction 4] The reaction was performed in the same procedure as described in Reaction 2 of Example 1 except that the product of Reaction 3 was used as a starting material. The yield was 74%.

[Reaction 5] The reaction was performed in the same procedure as described in Reaction 3 of Example 1 except that the product of Reaction 4 was used as a starting material. The yield was 90%.
<Analytical Data>

Molecular formula: $C_{27}H_{37}N_5O_7F_6$
1H-NMR (δppm): 2.3(m,CCH$_2$C), 2.8(m,CH$_2$N), 3.5(s, CH$_2$CO), 3.6(s,CH$_2$CO), 7.9-7.8(m,Φ)
$^{19}$F-NMR (δppm): -68.0
IR (vcm$^{-1}$): 2580-3400, 1720-1760(COOH, CONH), 1260(CF$_3$)

FAB-MS (M/Z): 658 (MH+)

[Reaction 6 (Synthesis of complex)] The reaction was performed in the same procedure as described in Reaction 4 of Example 1 except that the product of Reaction 5 was used as a starting material. The yield was 95% and 12.2 g of the end product were obtained. The overall yield was 30%.

EXAMPLE 18

Synthesis of gadolinium complex of 1-[2-[3,5-bis(trifluoromethyl)phenyl]ethyl]-1,4,8,11-tetraazacyclotetradecane-4,8,11-triacetic acid

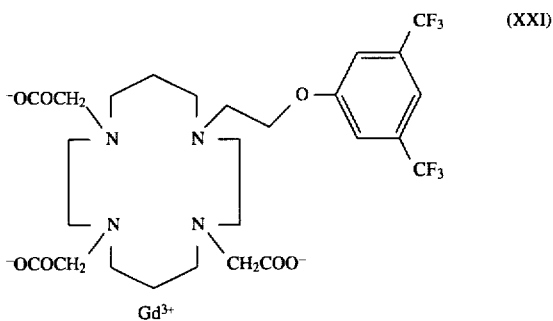

[Reaction 1] To a solution of 3,5-bis(trifluoromethyl)phenol in 300 ml of dimethylformamide, powdered sodiumhydride (5 g, 208 mmol) was added under cooling, and then, the resultant mixture was stirred at room temperature at 30 min. 113 g (600 mmol) of Ethyren dibromide was added quickly into the stirred reaction mixture, which was stirred further 2 hrs. at 80° C. The reaction mixture was evaporated to ¼ volume under reduced pressure and the residue was poured into ice cold water. The resultant aqueous solution was extracted with ethylacetate. The organic layer was washed with distilled water and saturated brine, and dried over sodiumsulfate. This was evaporated to concentrate under reduced pressure and the residue was purified by silica gel column chromatography eluted with ethylacetate/n-hexane=1/9. The yield was 72%.

[Reaction 2] The reaction was performed in the same procedure as described in Reaction 3 of Example 16 except that the product of Reaction 1 was used as a starting material. The yield was 83%.

[Reaction 3] The reaction was performed in the same procedure as described in Reaction 2 of Example 1 except that the product of Reaction 2 was used as a starting material. The yield was 72%.

[Reaction 4] The reaction was performed in the same procedure as described in Reaction 3 of Example 1 except that the product of Reaction 3 was used as a starting material. The yield was 93%.

<Analytical Data>

Molecular formula: $C_{26}H_{36}N_4O_7F_6$ $^1$H-NMR (δppm): 2.3(m,CCH$_2$C), 2.8(m,CH$_2$N), 3.5(s, CH$_2$CO), 3.6(s,CH$_2$CO), 3.9(m,CH$_2$O), 7.5–7.9(m,Φ)

$^{19}$F-NMR (δppm): −68.4

IR (vcm$^{-1}$): 2660–3430,1730–1780(COOH), 1260(CF$_3$), 1240(—O—)

FAB-MS (M/Z): 631 (MH+)

[Reaction 6 (Synthesis of complex)] The reaction was performed in the same procedure as described in Reaction of Example 1 except that the product of Reaction 4 was used as a starting material. The yield was 93% and 12.1 g of the end product were obtained. The overall yield was 37%.

EXAMPLE 19

Synthesis of gadolinium complex of 1-[2-[3,5-bis(trifluoromethyl)phenyloxy]ethyl]-1,4,8,11-tetraazacyclotetradecane-4,8,11-triacetic acid (compound 19, formula XXII)

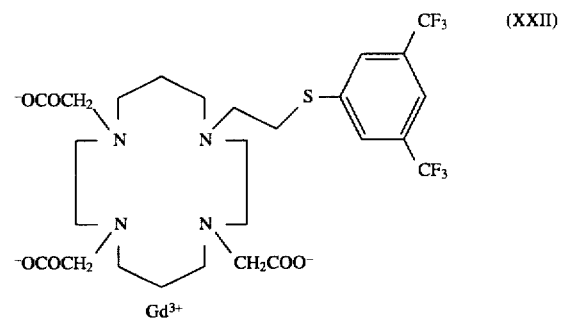

[Reaction 1] The reaction was performed in the same procedure as described in Reaction 1 of Example 18 except that 3,5-bis(trifluoromethyl)thiophenol was used in place of 3,5-bis(trifluoromethyl)phenol. The yield was 68%.

[Reaction 2] The reaction was performed in the same procedure as described in Reaction 3 of Example 16 except that the product of Reaction 1 was used as a starting material. The yield was 81%.

[Reaction 3] The reaction was performed in the same procedure as described in Reaction 2 of Example 1 except that the product of Reaction 2 was used as a starting material. The yield was 69%.

[Reaction 4] The reaction was performed in the same procedure as described in Reaction 3 of Example 1 except that the product of Reaction 3 was used as a starting material. The yield was 91%.

<Analytical Data>

Molecular formula $C_{26}H_{36}N_4O_6F_6S$ $^1$H-NMR (δppm): 2.3(m,CCH$_2$C), 2.3 (t,CH$_2$S), 2.8 (m,CH$_2$N), 3.5(s,CH$_2$CO), 3.6 (s,CH$_2$CO), 3.9 (m,CH$_2$O), 7.3–7.5(m,Φ)

$^{19}$F-NMR (δppm):
−68.0

IR (vcm$^{-1}$): 2600–3420, 1720–1740 (COOH), 1250 (CF$_3$)

FAB-MS (M/Z): 608 (MH+)

[Reaction 5 (Synthesis of complex)] The reaction was performed in the same procedure as described in Reaction 4 of Example 1 except that the product of Reaction 4 was used as a starting material. The yield was 90% and 11.6 g of the end product were obtained. The overall yield was 31%.

EXAMPLE 20

Synthesis of gadolinium complex of
1-[N"",N""-bis[3,5-bis(trifluoromethyl)benzyl]
aminoethyl]-1,4,8,11-
tetraazacyclotetradecane-4,8,11-triacetic acid
(compound 20, formula XXIII)

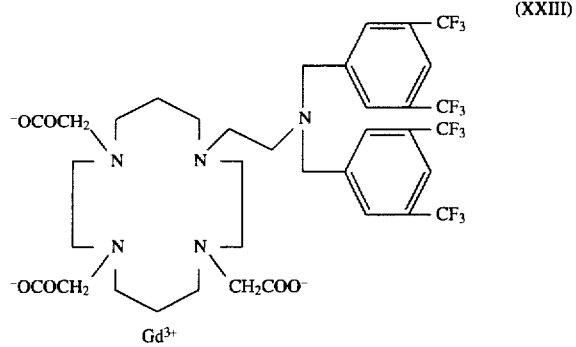

(XXIII)

[Reaction 1] To a solution of ethanolamine (12 g, 200 mmol) in 300 ml of dried tetrahydrofuran, 3,5-bis(trifluoromethyl)benzyl bromide (123 g, 400 mmol) was added. After refluxing under heating for 3 hrs., the reaction mixture was evaporated to concentrate under reduced pressure. 100ml of Ethylacetate was added into the residue and the resulting solution was washed twice with distilled water and once with saturated brine. This was purified by silica gel column chromatography 10 eluted with ethylacetate/n-hexane=3/7. The yield was 81%.

[Reaction 2] The product of Reaction 1 (83 g, 162 mmol) was dissolved in 100 ml of dried pyridine. Recrystallized p-toluenesulfonyl chloride (34 g, 178 mmol) was added at 0° C. over 1 hr and the mixture was stirred at room temperature for additional 1 hr. The reaction mixture was poured into ice-water and extracted with 2 l ethylacetate. The organic layer was washed twice with diluted hydrochloric acid, twice with distilled water, and once with saturated brine. The resultant solution was dried over anhydrous sodiumsulfate and evaporated to dryness under reduced pressure. The yield was 88%.

[Reaction 3] The reaction was performed in the same procedure as described in Reaction 3 of Example 16 except that the product of Reaction 2 was used as a starting material. The yield was 75%.

[Reaction 4] The reaction was performed in the same procedure as described in Reaction 2 of Example 1 except that the product of Reaction 3 was used as a starting material. The yield was 70%.

[Reaction 5] The reaction was performed in the same procedure as described in Reaction 3 of Example 1 except that the product of Reaction 4 was used as a starting material. The yield was 90%.

<Analytical Data>

Molecular formula: $C_{36}H_{43}N_5O_6F_{12}$ $^1$H-NMR ($\delta$ppm): 2.3(m,CCH$_2$C), 2.9(m,CH$_2$N), 3.5(s, CH$_2$CO), 3.6(s,CH$_2$CO), 7.7–7.9(m,$\Phi$)

$^{19}$F-NMR ($\delta$ppm): –68.3

IR (vcm$^{-1}$): 2600–3410, 1740–1760(COOH), 1210(CF$_3$)

FAB-MS (M/Z): 870 (MH$^+$)

[Reaction 6 (Synthesis of complex)] The reaction was performed in the same procedure as described in Reaction 4 of Example 1 except that the product of Reaction 5 was used as a starting material. The yield was 97% and 11.8 g of the end product were obtained. The overall yield was 33%.

EXAMPLE 21

Synthesis of gadolinium complex of
1-[N""-[3,5-bis(trifluoromethyl)benzyl]aminoethyl]-
1,4,8,11-tetraazacyclotetradecane-4,8,11-triacetic
acid (compound 21, formula XXIV)

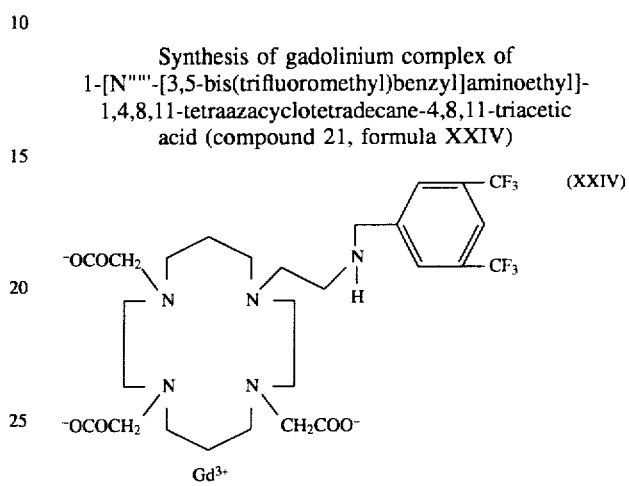

(XXIV)

[Reaction 1] The reaction was performed in the same procedure as described in Reaction 1 of Example 20 except that 123 g (400 mmol) of 3,5-bis(trifluoromethyl)benzyl bromide was used. The yield was 75%.

[Reaction 2] To a solution of the product of Reaction 1 (53 g, 19 4mmol) in 500 ml of chloroform containing 23 g (213 mmol) of triethylamine, o-nitrobenzyl bromide (48 g, 213 mmol) was added, and then, the resultant mixture was reflux under heating for 4 hrs. The reaction mixture was evaporated under reduced pressure and the residue was diluted with 300 ml of ethylacetate, washed twice with distilled water and once with saturated brine, then dried over anhydrous sodiumsulfate. This was purified by silica gel column chromatography eluted with ethylacetate/n-Hexane=3/7. The yield was 90%.

[Reaction 3] The reaction was performed in the same procedure as described in Reaction 2 of Example 20 except that the product of Reaction 2 was used as a starting material. The yield was 87%.

[Reaction 4] The reaction was performed in the same procedure as described in Reaction 3 of Example 16 except that the product of Reaction 3 was used as a starting material. The yield was 73%.

[Reaction 5] The reaction was performed in the same procedure as described in Reaction 2 of Example 1 except that the product of Reaction 4 was used as a starting material. The yield was 70%.

[Reaction 6] The reaction was performed in the same procedure as described in Reaction 3 of Example 1 except that the product of Reaction 5 was used as a starting material. The yield was 93%.

<Analytical Data>

Molecular formula: $C_{34}H_{43}N_5O_8F_6$ $^1$H-NMR ($\delta$ppm): 2.3(m,CCH$_2$C), 2.7(m,CH$_2$N), 3.3(s, CH$_2$CO), 3.4(s,CH$_2$CO), 7.7–7.9(m,$\Phi$)

$^{19}$F-NMR ($\delta$ppm): –67.8

IR (vcm$^{-1}$): 2610–3430, 1740–1780(COOH), 1230(CF$_3$)

FAB-MS (M/Z): 765 (MH$^+$)

[Reaction 7 (Synthesis of complex)] The reaction was performed in the same procedure as described in Reaction 4 of Example 1 except that the product of Reaction 6 was used as a starting material. The yield was 97%.

[Reaction 8] A solution of the product of Reaction 7 (12.5 g, 13 mmol) in 500 ml of methanol was hydrogenated over 10% palladium-carbon (1.0 g) under atmosphere pressure. After vigorously stirring for 5 hrs., the catalyst was removed by filtration. The filtrate was evaporated to ⅓ volume and diluted with isopropanol. A precipitate was collected by filtration. The obtained powder product was washed with small amount of isopropanol and dried under reduced pressure. The yield was 96% and 11.9 g of the end product were obtained. The overall yield was 34%.

EXAMPLE 22

Synthesis of gadolinium complex of 1-[N''''-[3,5-bis(trifluoromethyl)benzyl]aminoethyl]-1,4,8,11-tetraazacyclotetradecane-4,8,11,N''''-tetraacetic acid (compound 22, formula XXV)

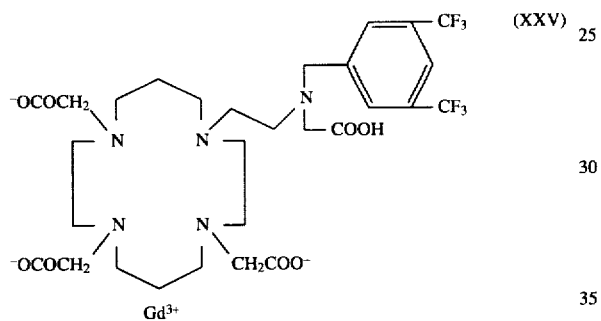

(XXV)

[Reaction 1] The reaction was performed in the same procedure as described in Reaction 2 of Example 21 except that 37 g (213 mmol) of bromoethylacetate was used instead of benzyl bromide. The yield was 75%. [Reaction 2] The reaction was performed in the same procedure as described in Reaction 2 of Example 20 except that the product of Reaction 1 was used as a starting material. The yield was 86%.

[Reaction 3] The reaction was performed in the same procedure as described in Reaction 3 of Example 16 except that the product of Reaction 2 was used as a starting material. The yield was 74%.

[Reaction 4] The reaction was performed in the same procedure as described in Reaction 2 of Example 1 except that the product of Reaction 3 was used as a starting material. The yield was 72%.

[Reaction 5] The reaction was performed in the same procedure as described in Reaction 2 of Example 1 except that the product of Reaction 4 was used as a starting material. The yield was 90%.
<Analytical Data>
Molecular formula: $C_{29}H_{41}N_5O_8F_6$
$^1$H-NMR (δppm): 2.3(m,CCH$_2$C), 2.7(m,CH$_2$N), 3.6(s, CH$_2$CO), 3.7(s,CH$_2$CO), 7.4–7.9(m,Φ)
$^{19}$F-NMR (δppm): –68.4
IR (vcm$^{-1}$): 2600–3450, 1730–1760(COOH), 1240(CF$_3$)
FAB-MS (M/Z): 702 (MH$^+$)

[Reaction 6 (Synthesis of complex)] The reaction was performed in the same procedure as described in Reaction of Example 1 except that the product of Reaction 5 was used as a starting material. The yield was 95% and 12.1 g of the end product were obtained. The overall yield was 38%.

EXAMPLE 23

Synthesis of copper complex of 1-[3,5-bis(trifluoromethyl)benzyl]-1,4,8,11-tetraazacyclotetradecane-4,8,11-triacetic acid (compound 23, formula XXVI)

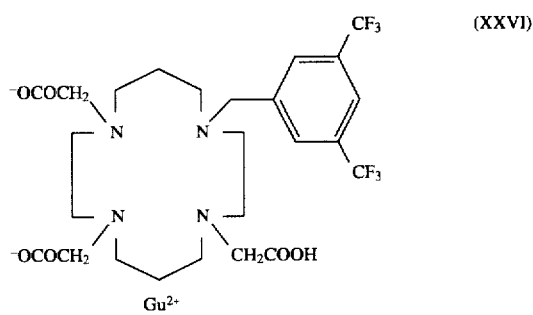

(XXVI)

[Reaction 1] 10 g (17 mmol) of the ligand compound obtained by Reaction 6 of Example 1 were dissolved in distilled water containing 1N sodium hydroxide, and 2.7 g (33 mmol) of cupric oxide was added to the solution. After stirring at 80° C. for 3 hrs., the unreacted cupric oxide was removed by filtration. The filtrate was treated by a cation exchange resin (Amberlite, IR-120B) and evaporated to dryness under reduced pressure. 11.2 g of the end product were obtained. The yield of this reaction was 98% and overall yield was 41%.

EXAMPLE 24

Synthesis of chromium complex of 1-[3,5-bis(trifluoromethyl)benzyl]-1,4,8,11-tetraazacyclotetradecane-4,8,11-triacetic acid (compound 24, formula XXVII)

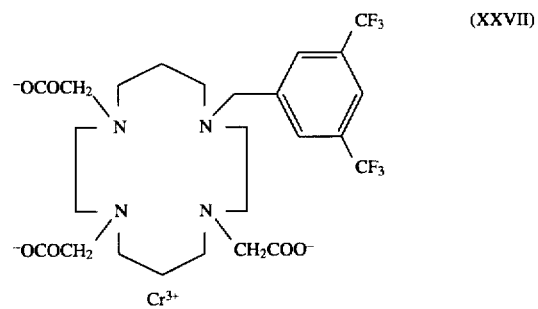

(XXVII)

[Reaction 1] The reaction was performed in the same procedure as described in Reaction 1 of Example 23 except that 2.6 g (17 mmol) of chromium(III) oxide was used in place of cupric oxide. The yield was 96% and 11.4 g of the end product were obtained. The overall yield was 40%.

EXAMPLE 25

Synthesis of manganese complex of 1-[3,5-bis(trifluoromethyl)benzyl]-1,4,8,11-tetraazacyclotetradecane-4,8,11-triacetic acid (compound 25, formula XXVIII)

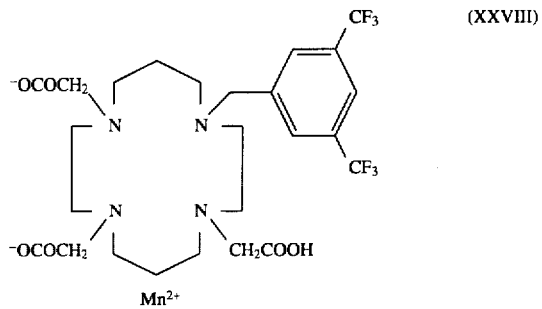

(XXVIII)

[Reaction 1] The reaction was performed in the same procedure as described in Reaction 1 of Example 23 except that 2.8 g (33 mmol) of manganese dioxide was used in place of cupric oxide. The yield was 97% and 11.4 g of the end product were obtained. The overall yield was 41%.

EXAMPLE 26

<measurement of relaxation time>

Each metal complex of the present invention was prepared into a 10mM aqueous solution, and the $T_1$ and $T_2$ values of intramolecular fluorine atoms contained in the solution was measured by using 90 MHz-NMR (EX-90, manufactured by JEOL). The result is shown in Table 1.

TABLE 1

| Compound | T1 | T2 | Compound | T1 | T2 |
| --- | --- | --- | --- | --- | --- |
| Compound-1 | 1.73 | 1.58 | Compound-13 | 12.6 | 9.31 |
| Compound-4 | 2.16 | 1.82 | Compound-21 | 6.34 | 4.21 |
| Compound-8 | 2.11 | 1.79 | Compound-23 | 36.5 | 24.9 |
| Compound-10 | 3.27 | 2.83 | Compound-24 | 15.5 | 10.4 |

EXAMPLE 27

Measurement of imaging sensitivity (phantom experiment)

Each of metal complex solution with various concentration of the present invention was sealed in cylindrical acryl phantom with an inner diameter of 1 cm and a height of 10 cm and subject to imaging. SIGNA (1.5 T) available from GE was used as an MRI apparatus, and imaging was performed by using a surface coil 13 cm in diameter for fluorine. A GRASS method was used as a pulse sequence and measurement condition was as followed:

TR (repetition time)=10 msec;
TE (echo time)=2 msec;
FA(flip angle)=90 deg.;
slice width=2.0 cm;
matrix size=256×128.

The measurement was performed for 20 min., and the number of acquisition was 937. As references, alkaline aqueous solutions of 5-fluorouracil with various concentrations were imaged by an identical apparatus. Condition for obtaining the highest imaging sensitivity were examined and were found to be a spin echo method as the pulse sequence, TR=4500 msec, TE=100 msec. The imaging time was 20 min., and the number of acquisition was twice. The result are shown in Table 2 below. As can be seen from Table 2, it was impossible to detect the aqueous 5-fluorouracil solution as a clear image unless the concentration of the solution was 500 mM or more. In contrast, each metal complex compound of the present of the minimum of 0.5 mM to 5 mM. Other compounds of the present invention not recited in Table 2 also exhibited substantially the same sensitivities.

TABLE 2

| Compound | Concentration | | | | | | | |
| --- | --- | --- | --- | --- | --- | --- | --- | --- |
| | 500 mM | 100 mM | 50 mM | 10 mM | 5 mM | 1 mM | 500 µM | 100 µM |
| 5-FU | o | Δ | Δ | x | x | x | x | x |
| Compound-3 | o | o | o | o | Δ | Δ | x | x |
| Compound-4 | o | o | o | o | o | o | Δ | x |
| Compound-5 | o | o | o | o | o | o | Δ | x |
| Compound-13 | o | o | o | o | o | Δ | x | x |
| Compound-20 | o | o | o | o | o | o | Δ | Δ |
| Compound-23 | o | o | o | o | o | Δ | x | x |

(5-FU: 5-fluorouracil as reference sample)
o: detectable as clear image
Δ: marginally detectable as image
x: undetectable

EXAMPLE 28

Metal complex compound labeling reaction of monoclonal antibody

To a solution of compound 21 (7.0 mg, 10.3 µmol) in a carbonate buffer (pH=8.0), 2.5 mg (13.1 µmol) of N-(dimethylaminopropyl)-N'-ethylcarbodiimide was added at 0° C., followed by adding 2 mg of anti-CEA monoclonal antibody (mouse IgG 1 available from Japan Biotest Laboratory) dissolved in 1 ml PBS. The solution was reacted at room temperature for 2 hrs. Excess reagent and unreacted component were removed by dialysis against phosphoric acid buffer solution and by performing centrifugal separation several times. The resultant preparation was purified through Sephadex G-400 column and freeze-dried. A labeling ratio was calculated from a gadolinium quantity measured by ICP and a protein quantity determined by a Lowly method. The result was a composite in which 9.8 molecules of the compound 21 were bonded to each antibody on average.

EXAMPLE 29

Imaging of tumor tissue using mouse

The compound-21 coupled with the anti-CEA antibody which was prepared in Example 28 was dissolved in PBS containing a small amount of mouse serum albumin and the solution was adjusted to have a gadolinium concentration of 1 mM. 2.0 ml of Resultant solution were intravenously injected into a nude mouse to which a human carcinoma of the colon and rectum was transplanted. After 24 hrs. from the injection, MRI imaging was performed under same condition as in Example 28. As a control experiment, a similar anti-CEA antibody which was 131-iodine labeled by a chloramine T method was given to a mouse in the same manner as described above, and imaging was performed by using a gamma camera (STARCAM available from GE) at the time 24 hrs. after injection.

As a result the tumor could be detected as a clear image by the method using the metal complex compound of the present invention, and almost no image artifact was found. In addition the contrast with respect to the background was higher than and the image resolution was much higher than those of the control experiment performed by means of nuclear medicine.

EXAMPLE 30

Acute toxicity experiment of contrast medium of the present invention

Each of the contrast medium compounds of the invention was dissolved in distilled water for injection to afford 1M solution. To the resultant solution, tromethamine was added for adjusting pH to 7.5, and then, disodium ethylendiamin-tetraacetate was added so that concentration thereof is 0.05% (w/v). Ampoules are dispensed with 20 ml of the resultant solution and sterilized in an autoclave at 120° C. for 10 minutes, thereby obtaining MRI-diagnosis reagents.

The MIR-diagnosis reagents were intravenously injected for examining acute toxicity thereof. As a result, $LD_{50}$ values much larger than a clinical dose were obtained and the high safety of the reagents were established.

What is claimed is:

1. A $^{19}$F-MRI contrast medium for MRI using $^{19}$F as a detectable nucleus, comprising a metal complex compound in which a macro-cyclic polyamine ligand containing not less than one fluorine atom is coordinate-bonded to a paramagnetic metal ion and wherein said metal complex compound is a member selected from the group consisting of a metal complex compound represented by the following formula (I) and a physiologically acceptable salt thereof;

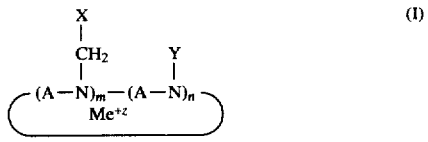
(I)

wherein Me, z, A, m, X, n, and Y have the following meanings;

Me: paramagnetic metal ion z: the ionic valence of Me, a positive integer

A: which may be the same or different and each represent a group selected from the group consisting of straight chain or branched chain alkylene groups having 1 to 6 carbon atoms, —$(CH_2)_l$—O—$(CH_2)_l$—, and —$(CH_2)_l$—CO—$(CH_2)_l$—, where l is an integer from 1 to 6 m: an integer from 1 to 6 x: which may be the same or different and each represents a group selected from the group consisting of —COOZ, —$PO_3HZ$, —CONHW, and —OH where Z and W are;

Z: a hydrogen atom, an organic or inorganic base equivalent or metal (Me) ion equivalent W: a straight chain or branched chain alkyl group substituted with not less than one —OH group n: an integer from 1 to 6

Y: when n=1, Y is R, wherein R is a substituent which contains not less than one fluorine atom and may contain X defined above, and when n=2 or 3, at least one Y is R as defined above and each of remaining Y members is —$CH_2X$, a lower alkyl group, or a hydrogen atom and wherein a macro-cyclic polyamine ligand portion of the metal complex compound is coordinate-bonded to the paramagnetic metal ion via at least one of the nitrogen atoms and/or oxygen atoms which are contained in the ligand.

2. The contrast medium according to claim 1, wherein said paramagnetic metal is a member selected from the group consisting of chromium, manganese, iron, copper, and gadolinium.

3. The contrast medium according to claim 1, wherein said macro-cyclic polyamine ligand contains a plurality of fluorine atoms.

4. The contrast medium according to claim 3, wherein NMR chemical shifts of said plurality of fluorine atoms are essentially the same.

5. The contrast medium according to claim 4, wherein all of the NMR chemical shifts of said plurality of fluorine atoms are distributed within a range of not broader than 30 ppm.

6. The contrast medium according to claim 1, wherein a tissue specific substance with a specific affinity for a particular living tissue to be imaged is bonded to said macro-cyclic polyamine ligand.

7. The contrast medium according to claim 6, wherein said tissue specific substance is bonded to said macro-cyclic polyamine ligand via a suitable linker.

8. The contrast medium according to claim 6, wherein said tissue specific substance is a substance comprising a peptide and/or a carbohydrate.

9. The contrast medium according to claim 6, wherein said tissue specific substance is a monoclonal antibody.

10. The contrast medium according to claim 1, further comprising assistants or additives normally used in pharmaceutics and selected from fillers, stabilizers, surfactants, buffering agents, electrolytes, coloring agents, flavoring agents, and taste-conditioning agents, wherein said contrast medium is prepared into a tablet, a powdered medicine, or a liquid medicine.

11. The contrast medium according to claim 1, wherein said —R is —$R_{1F}$, wherein —$R_1F$ means a straight chain or branched chain alkyl group which is substituted with not less than one fluorine atom and may contain X defined above.

12. The contrast medium according to claim 1, wherein said —R is a member selected from the group consisting of

—$R_1F$;

—$R_2$—$Ar_F$, —$R_2$—Φ—$R_2$—$Ar_F$;

—$SO_2$—$R_{1F}$, —$SO_2$—$R_2$—$R_{1F}$, —$SO_2$—$Ar_F$, —$SO_2$—$R_2$—$Ar_F$;

—CO—$R_{1F}$, —CO—$R_2$—$R_{1F}$, —CO—$Ar_F$, —CO—$R_2$—$Ar_F$;

—$R_2$—NH—$SO_2$—$R_{1F}$, —$R_2$—NH—$SO_2$—$Ar_F$, —$R_2$—NH—$SO_2$—$R_2$—$Ar_F$;

—$R_2$—$SO_2$—NH—$R_{1F}$, —$R_2$-$SO_2$—NH—$Ar_F$, —$R_2$—$SO_2$—NH—$R_2$—$Ar_F$;

—$R_2$—NH—CO—$R_{1F}$, —$R_2$—NH—CO—$Ar_F$, —$R_2$—NH—CO—$R_2$—$Ar_F$;

—$R_2$—CO—NH—$R_{1F}$, —$R_2$—CO—NH—$Ar_F$, —$R_2$—CO—NH—$R_2$—$Ar_F$;

—$R_2$—S—$R_{1F}$, —$R_2$—S—$Ar_F$, —$R_2$—S—$R_2$—$Ar_F$;
—$R_2$—O—$R_{1F}$, —$R_2$—O—$Ar_F$, —$R_2$—O—$R_2$—$Ar_F$;
—$R_2$—NH—$R_{1F}$, —$R_2$—NH—$R_2$—$Ar_F$;
—$R_2$—N($R_3$)—$R_{1F}$, —$R_2$—N($R_3$)—$R_2$—$Ar_F$;
—$R_2$—N(X)$R_{1F}$, —$R_2$—N(X)—$R_2$—$Ar_F$;
—$R_2$—N($R_1$F)—$R_2$—$Ar_F$, and
—$R_2$—N($R_2$—$Ar_F$)$_2$, and wherein each of X and —$R_{1F}$ represents the same meaning as defined above, and —$R_2$—, —$R_3$, —Φ—, and —$Ar_F$ have the following meanings;

—$R_2$—: a saturated or unsaturated hydrocarbon chain
—$R_3$: a lower alkyl group
—Φ—: a phenylene group
—$Ar_F$: a group represented by the following formula

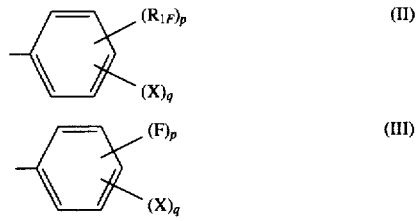

(p represents an integer from 1 to 5, and q represents 0 or an integer from 1 to 4).

13. A method of MRI analysis which method comprises the detection of $^{19}$F which uses a $^{19}$F-MRI contrast medium according to claim 1.

14. The method of claim 13, wherein the MRI method is used to image specific tissues in a subject.

15. The method of claim 13, wherein the method is used to detect specific changes in tissue environments.

16. The method of claim 15, wherein said changes include changes in pH, changes in oxygen concentration, and/or changes in oxidation/reduction potential.

17. The method of claim 14, wherein said method is used to identify tumor tissues.

18. The method of claim 14, wherein said method is used to identify an infarct portion of a blood vessel.

19. The method of claim 14, wherein said method is used to identify ischemic tissue.

20. The method of claim 13, wherein the contrast medium is used to coat a catheter or artificial organ and MRI is effected to identify the position of the catheter or artificial organ in a subject.

21. The method of claim 13, which is used to map receptors and which method uses a tissue specific substance selected from the group consisting of antibodies, agonists, antagonists, hormones, chemical transmitters and anti-receptor antibodies.

22. The method of claim 13, which is used to diagnose a disease condition selected from the group consisting of cancer, infectious disease, ischemic heart disease, arterial sclerosis, ulcers and mental disease.

* * * * *

UNITED STATES PATENT AND TRADEMARK OFFICE
CERTIFICATE OF CORRECTION

PATENT NO. : 5,536,491
DATED : July 16, 1996
INVENTOR(S) : Hiroyuki Asai and Tetsuro Kawanishi It is certified that error appears in the above-indentified patent and that said Letters Patent is hereby corrected as shown below:

On title page,

In Section [75] correct second inventor's name to read --Kawanishi--.

In the Abstract, line 6, kindly delete "$^{19}$-F-MRI" and insert --$^{19}$F-MRI--.

In Column 6, line 10, delete "T2" and insert --$T_2$--.

In Column 11, line 31, delete "$_{-R2}$" and insert ----$R_2$--.

In Column 11, line 50, delete "formula" and insert --formula (II) or (III)--.

In Column 17, line 65, delete "Reaction" and insert --Reaction 4--.

In Column 19, line 25, delete "2.8" and insert --12.8--.

In Column 20, line 63, delete "Reaction" and insert --Reaction 4--.

In Column 22, line 18, delete "Reaction" and insert --Reaction 4--.

In Column 26, line 36, delete "retool" and insert --mmol--.

In Column 27, line 50, delete "10".

In Column 28, line 5, delete "Reaction" and insert --Reaction 4--.

In Column 29, line 35, delete "10".

In Column 31, line 40, delete "[Reaction 2] The".

In Column 31, line 41, insert --[Reaction 2] The--.

In Column 31, line 66, delete "Reaction" and insert --Reaction 4--.

In Claim 11, line 2, delete "-$R_1F$" and insert --$R_{1F}$--.

In Claim 12, line 11, delete "$_{-R2}$" and insert ----$R_2$--.

UNITED STATES PATENT AND TRADEMARK OFFICE
CERTIFICATE OF CORRECTION

PATENT NO. : 5,536,491
DATED : July 16, 1996
INVENTOR(S) : Hiroyuki Asai and Tetsuro Kawanishi It is certified that error appears in the above-indentified patent and that said Letters Patent is hereby corrected as shown below:

In Claim 12, line 22, delete "$R_1F$" and insert --$R_{1F}$--.

Signed and Sealed this

Seventeenth Day of June, 1997

*Attest:*

BRUCE LEHMAN

*Attesting Officer*    Commissioner of Patents and Trademarks